US006765089B1

(12) United States Patent
Toth et al.

(10) Patent No.: US 6,765,089 B1
(45) Date of Patent: *Jul. 20, 2004

(54) PROTECTING AND LINKING GROUPS FOR ORGANIC SYNTHESIS ON SOLID SUPPORTS

(75) Inventors: Istvan Toth, Sherwood (AU); Gyula Dekany, Ruislip (GB); Barry Kellam, Maidstone (GB)

(73) Assignee: Alchemia Pty Ltd, Sherwood (AU)

(*) Notice: Subject to any disclaimer, the term of this patent is extended or adjusted under 35 U.S.C. 154(b) by 0 days.

This patent is subject to a terminal disclaimer.

(21) Appl. No.: 09/509,105

(22) PCT Filed: Sep. 24, 1998

(86) PCT No.: PCT/AU98/00808

§ 371 (c)(1),
(2), (4) Date: Mar. 20, 2000

(87) PCT Pub. No.: WO99/15510

PCT Pub. Date: Apr. 1, 1999

(30) Foreign Application Priority Data

Sep. 24, 1997 (AU) .......................................... PO 9375

(51) Int. Cl.$^7$ ............................................. C07H 15/00
(52) U.S. Cl. ..................... 536/17.6; 536/18.7; 536/124; 536/1.11; 544/299; 568/327
(58) Field of Search ............................... 536/17.6, 1.11, 536/124, 18.7; 544/299; 568/327

(56) References Cited

U.S. PATENT DOCUMENTS

| | | | | |
|---|---|---|---|---|
| 3,828,043 A | * | 8/1974 | Kay et al. .................... | 544/299 |
| 3,999,974 A | * | 12/1976 | Hirono et al. ............... | 514/270 |
| 4,062,950 A | | 12/1977 | Frommer et al. ............ | 514/36 |
| 4,229,454 A | * | 10/1980 | Beriger ........................ | 514/270 |
| 4,239,762 A | * | 12/1980 | Krämer et al. .............. | 514/270 |
| 4,283,444 A | * | 8/1981 | de Sousa et al. ........... | 427/421 |
| 4,502,861 A | * | 3/1985 | Becker et al. ................. | 8/490 |
| 4,503,100 A | * | 3/1985 | de Sousa et al. ........... | 427/428 |
| 4,602,912 A | * | 7/1986 | de Sousa et al. ............ | 8/127.5 |
| 4,742,124 A | * | 5/1988 | Frisch et al. ................. | 525/124 |
| 4,748,178 A | * | 5/1988 | Burckhardt et al. ........ | 514/270 |
| 4,753,940 A | * | 6/1988 | Sturm et al. ................. | 514/252 |
| 4,762,830 A | * | 8/1988 | Sturm et al. ................. | 514/270 |
| 4,797,147 A | * | 1/1989 | Lee et al. ...................... | 71/92 |
| 4,938,796 A | * | 7/1990 | Buren et al. .................... | 71/98 |
| 5,162,327 A | * | 11/1992 | Kratt et al. .................. | 514/270 |
| 5,959,109 A | * | 9/1999 | Whitten et al. .............. | 544/311 |
| 6,133,276 A | * | 10/2000 | Whitten et al. .............. | 514/270 |
| 6,335,332 B1 | * | 1/2002 | Oliva et al. ............... | 514/227.8 |
| 6,462,183 B1 | | 10/2002 | Toth et al. ................... | 536/17.2 |
| 6,573,337 B1 | * | 6/2003 | Toth et al. ................. | 525/333.6 |

FOREIGN PATENT DOCUMENTS

| | | |
|---|---|---|
| EP | 0 169 168 A1 | 1/1986 |
| WO | WO 97/45421 | 12/1997 |
| WO | WO98/08799 | 3/1998 |
| WO | WO98/14423 | 4/1998 |
| WO | WO98/38197 | 9/1998 |
| WO | WO 99/15510 A1 | 4/1999 |
| WO | WO 00/42057 A1 | 7/2000 |

OTHER PUBLICATIONS

Sofia, M., "Chemical Strategies for Introducing Carbohydrate Molecular Diversity into the Drug Discovery Process," *Network Science*—WEB published only, issue of Jun./Jul., 1996; Retrieve at URL: http://www.netsci.org/Science/Combichem/feature12.html.

Liu et al., "Synthesis of Thermochromic Spiroindolinebenzopyran–6'–methylenebarbituric Acid," *Xibei Daxue Xuebao, Ziran Kexueban*, 28(6), 506–508 (1998†, Chinese); *Chemical Abstracts*, 131(11), p. 843, Abstract No. 145669h (Sep. 13, 1999); CAPlus–generated structure included on a separate page; only abstract supplied.

Bolvag et al., "Tautomerism of Enolic Triacetylmethane, 2–Acyl–1,3–cycloalkanediones, 5–Acyl Meldrum's Acids and 5–Acyl–1,3–dimethyl–barbituric Acids Studied by Means of Deuterium Isotope Effects on $^{13}$C Chemical Shifts," *Magnetic Resonance in Chemistry*, 36(5), 315–324 (1998).

Alonso, et al., "Cytostatic Quinones. II. Synthesis of N–Glycosyl Heterocyclic Quinones," *Eur. J. Med. Chem.–Chimica Therapeutica*, 13(2):155–160, (Mar.–Apr., 1978).

Bycroft, et al., "Synthesis of the Spider Toxins Nephilatoxin–9 and—11 by a Novel Solid–Phase Strategy," *J. Am. Chem. Soc.*, 116:7415–7416, 1994. (Issue No. 16), Month of publication data is unavailable for this reference.

Bycroft, et al., "A Novel Lysine–Protecting Procedure for Continuous Flow Solid Phase Synthesis of Branched Peptides," *J. Chem. Soc. Chem. Commun.*, 778–779, 1993, Month of publication data is unavailable for this reference.

Chan, et al., "A Novel 4–Aminobenzyl Ester–Based Carboxy–Protecting group for Synthesis of Atypical Peptides by Fmoc–Bu$^t$ Solid–Phase Chemistry," *J. Chem. Soc. Chem. Commun.*, 2209–2210, 1995, Month of publication data is unavailable for this reference.

Chan, et al., "Novel Protecting Group for Fmoc/tBu Solid–Phase Synthesis of Side–Chain Carboxy Modified Peptides," *Chemical Abstracts*, 126:8616; *Pept.*, 1994; *Proc. Eur. Pept. Symp.*, 1995., Leiden, Netherlands. (1998), Month of publication data is unavailable for this reference.

(List continued on next page.)

*Primary Examiner*—James O. Wilson
*Assistant Examiner*—Lawrence Crane
(74) *Attorney, Agent, or Firm*—Williams, Morgan and Amerson

(57) ABSTRACT

This invention relates to methods for synthesis of organic compounds, and in particular to compounds useful as protecting and linking groups for use in the synthesis of peptides, oligosaccharides, glycopeptides and glycolipids. The invention provides protecting and linking groups that are useful in both solid phase and solution synthesis, and are particularly applicable to combinatorial synthesis.

23 Claims, No Drawings

OTHER PUBLICATIONS

Grigg, et al., "X:Y–ZH Systems as Potential 1, 3–Dipoles Part 9,", *Chemical Abstracts,* 109:211406; *J. Chem. Soc., Perkin Trans. I,* 3:541–544, 1988, Month of publication data is unavailable for this reference.

Gudriniece, et al., "2–Aminomethylene–1, 3–Indandione and its Reactions with Amino Acids," *Chemical Abstracts,* 92:215102, *Latv. PSR Zinat. Akad. Vestis., Kim. Ser.,* :713–716, 1979, (Iss. No. 6), Month of publication data is unavailable for this reference.

Jure, et al., "Synthesis and Cytokine Activity of Some 6–Methinoaminopurine Derivatives," *Chemical Abstracts,* 114:23660, *Latv. PSR Zinat. Akad. Vestis., Kim. Ser.,* 445–453, 1990, (Iss. No. 4), Month of publication data is unavailable for this reference.

Palacios, et al., "1, 3–Dipolar Cycloaddition of Azidoalkyl Phosphonates and –Carboxylates to Maleimide and Naphthoquinone," *Chemical Abstracts,* 124:202402; *Org. Prep. Proced. Int.,* 27(6):625–635, 1995. (1998), Month of publication data is unavailable for this reference.

International Search Report, Serial No. PCT/AU98/00808, published Apr. 1, 1999, Month of publication data is unavailable for this reference.

Ding et al., "Synthesis and Biological Activity of Oligosaccharide Libraries", *Glycoimmunology Plenum Press.* 261–269, 1995, Month of publication data is unavailable for this reference.

Garcia Martin et al., "Glycosides of 1–amino–1–deoxy–D––fructose," *Carbohydrate Res.,* 199:139–151, 1990, Month of publication data is unavailable for this reference.

Kellam, et al., "Solid phase strategies: applications of 2–acetyl–4–nitroindane–1, 3– dione as a selective protecting group for primary amines," *Tetrahedron,* 54:6817–6832, (Jun. 11, 1998), Month of publication data is unavailable for this reference.

Liang, et al., "Parallel synthesis and screening of a solid phase carbohydrate library," *Science,* 274:1520–1522, (Nov. 29, 1996), Month of publication data is unavailable for this reference.

Protecting Groups in Organic Synthesis, ed. Green & Wuts, John Wiley & Sons, pp. 591–592, 1999, New York, NY, Month of publication data is unavailable for this reference.

Akhrem et al., "Reaction of some aromatic oxides of nitriles with dimedone," *Khim Geterotsikl.* Soedin, 7:901–904, cited in CAPLUS as 1974:505372, Chem Abstr. 81, 105372(1974), Month of publication data is unavailable for this reference.

International Search Report from Hungarian Patent Office for Patent Application No. P0000819, dated Dec. 20, 2000, mailed to client Jan. 31, 2001, received by client Mar. 21, 2001, published Aug. 31, 2001.

Wipfler et al., "The Reactivity of the C=N–Double Bond System, XV[1] The Reaction of Anilinomethylene–Barbituric Acids with Methylenactive Nitriles"; *Z. Naturforsch,* 33b:1016–1019, 1978, with Translation. (Sep., 1978).

Supplemental Partial European Search Report for Patent Application No. EP 98 94 6145.4 dated Jan. 23, 2002.

* cited by examiner

PROTECTING AND LINKING GROUPS FOR ORGANIC SYNTHESIS ON SOLID SUPPORTS

The present application is a nationalization of International Patent Application PCT/AU98/00808, filed Sep. 24, 1998, which claims priority to Australian Patent Application PO 9375, filed Sep. 24, 1997 and to U.S. Provisional Application Serial No. 60/061,987, filed Oct. 14, 1997, now abandoned.

FIELD OF THE INVENTION

This invention relates to methods for synthesis of organic compounds, and in particular to compounds useful as protecting and linking groups for use in the synthesis of peptides, oligosaccharides, glycopeptides and glycolipids. The invention provides protecting and linking groups which are useful in both solid phase and solution synthesis, and are particularly applicable to combinatorial synthesis.

BACKGROUND OF THE INVENTION

The problem of functional group incompatibility in the synthesis or complex organic structures demands the use of a functional group protection strategy. Complex synthetic intermediates and products usually contain a multiplicity of reactive groups, most of which must first be blocked, and subsequently liberated at an appropriate point in the synthesis. The problem is especially acute in the design and construction of polyfunctional molecules such as oligosaccharides, peptides, glycopeptides and glycolipids.

In oligosaccharide synthesis, a variety of protective groups are required. It is necessary to place groups regioselectively at specific locations; on primary alcohols, on cis-diols, on trans-diols, on 1,2-diols, on 1,3-diols, or on particular secondary alcohols. In addition, aminosugars are important constituents of oligosaccharides, and their aminoprotection should be compatible with the hydroxy group protection strategy. The properties of the protective group adjacent to the anomeric centre are also important. Whether this group is participating or non-participating plays a significant role in control of glycoside stereochemistry. Because most reactions at the glycosidic centre proceed via electron deficient intermediates, electron-releasing substituents on the C-2 substituent accelerate the reaction at the glycosidic centre. Electron-withdrawing substituents, normally esters or amides, slow the reaction. In solid phase oligosaccharide synthesis, the stability and sensitivity of the linker between the first sugar unit and the resin becomes a crucial part of the protection plan. The presence of other functional groups, such as alkenes or esters, or features such as a furanose ring in the target oligosaccharide, may dictate that the protecting groups used for the synthesis are not sensitive to acid, base, reductive, or other commonly used cleavage techniques. The choice of protecting groups is therefore one of the decisive factors in the successful realization of solid phase oligosaccharide synthesis.

In solid phase peptide and glycopeptide synthesis the demand of a new orthogonal protective set is significant. The established orthogonal deprotection sets are based upon the well-known Fmoc and Boc protection of amino acids. The construction of complex peptides or glycopeptides often requires a third orthogonal protecting group for side-chain amino functionalities, whose removal will not affect the protecting groups in the other orthogonal sets, or vice versa.

Many protecting groups have been developed for amino group protection, and fall into seven broad classes.

1. N-Acyl Derivatives
   a) Phthalimides are especially useful in the protection of amino functions in aminoglycoside synthesis (Nicolaou et al, 1992), because they are stable during the glycosylation, and because they help to control the stereochemistry by neighbouring group participation. Unfortunately, the deprotection needs vigorous conditions, which often results in partial product decomposition.
   b) Trifluoroacetamides (Weygand and Czendes, 1952) Simple amide derivatives are usually worthless as protecting groups because the conditions required to remove them are too harsh. However, the trifluoroacetamide group is exceptionally labile to base hydrolysis, and is therefore useful in the protection of amines.
   c) Carbamates are used as protective groups for amino acids to minimize racemization in peptide synthesis. Racemization occurs during the base-catalysed coupling reaction of an N-protected, carboxyl-activated amino acid, and takes place via the intermediate oxazolone that forms readily from an N-acyl protected amino acid. Many carbamates, for example Boc (McKay and Albertson, 1957), Cbz (Bergman and Zervas, 1932), Alloc (Kunz and Unverzagt, 1984), Teoc (Carpino et al, 1978), and Troc (Windholz and Johnston, 1967), have been used as protective groups for amino protection.
2. N-Sulfonyl Derivatives
   Sulfonamide derivatives are frequently used in nitrogen heterocycles (Gribble et al, 1992), and arylsulfonyl (Fischer and Livschitz, 1915) groups are effective protective groups for a wide range of primary and secondary amines, but their deprotection requires drastic conditions. β-(Trimethylsilyl) ethanesulfonyl (Weinreb et al, 1986) derivatives are as stable as arylsulfonyl groups, but the cleavage step requires only gentle warming with TBAF or CsF.
3. N-Sulfenyl Derivatives
   Sulfenamides are much more labile than sulfonamides, being sensitive to acids as well as to attack by nucleophiles. Their deprotection requires exceptionally mild conditions. Several sulfenyl groups are used for the protection of the amino function including tritylsulfenyl (Brandchaud, 1983), o-nitrophenylsulfenyl (Goerdeler and Holst, 1959), and pentachlorphenylsulfenyl (Kessler and Iselin, 1966).
4. N-Alkyl Derivatives
   Benzylamines give useful protection in reactions in which metal hydrides are used and the carbamates are not stable. Benzylamines are less susceptible to catalytic hydrogenolysis than benzyl ethers or benzyl esters, and thus selective deprotection can often be achieved (Goldstein et al, 1992). The trityl group (Sieber and Riniker, 1991) is used to protect amino acids, although its steric bulk and high acid lability is detrimental to peptide coupling. The 9-phenylfluorenyl (PhFl; Koskinen and Rapoport, 1989) group is used for the protection of primary and secondary amines. Its hydrophobicity, steric bulk and ease of introduction are similar to the trityl group, but the PhFl group is about 6000 times more stable to acid than the trityl group.
5. N-Silyl Derivatives
   The high acid and moisture sensitivity of silylamines has been a major obstacle to their use in amino group protection. Butyldiphenylsilylamines (Overman and Okazaki, 1986) have remarkable stability towards strong basic conditions, but they are still very acid labile.
6. Imine Derivatives
   The double bond of the imine function allows for the simultaneous protection of both N—H bonds of a primary amine. Imines are generally stable towards strongly basic conditions, but they are labile to aqueous acid. N-Silyl imines (Colvin et al, 1988), N-bis(methylthio) methyleneamines (Hoppe and Beckmann, 1979) and N-diphenylmethyleneamines (Polt et al, 1979) are valuable for the protection of amino groups in the synthesis of α-amino acids.

7. Enamine Derivatives

N-(5,5-Dimethyl-3-oxo-1-cyclohexenyl)amine (Halpern and James, 1964) is used to protect amino acids, giving vinylogous amide derivatives. These compounds can be cleaved by treatment with either aqueous bromine or nitrous acid. The stability of the vinylogous amide-protected primary amines mainly depends on the structure of 1,3-dione and the functional group attached to the enamine double bond. The open chain N-(4-oxopent-2-enyl)-protected amines are labile towards aqueous and mildly acidic conditions. This acid sensitivity limits their use as synthetic reagents (Kellam, 1996). The cyclic 1,3-diketone, 5,5-dimethylcyclohexane-1,3-dione (dimedone) reacts with dimethylformamide dimethylacetal affording 5,5-dimethyl-2-(dimethylaminomethylene)cyclohexane-1,3-dione. Bycroft et al (1993) used this reagent to synthesise Dmc-protected α-amino acids, and found remarkable stability towards acidic conditions. The deprotection of these compounds could be rapidly achieved by a dilute hydrazine solution at room temperature. The introduction of a methyl group to the enamine double bond provided the N-1-(4,4-dimethyl-2,6-dioxocyclohexylidene)ethyl Dde-protective group, improving the stability towards secondary amines (Bycroft et al, 1993). The N-1-(4,4-dimethyl-2,6-dioxocyclohexylidene)-3-methylbutyl-protected amino acids (Chan et al, 1995), carrying a bulkier group at the enamine double bond, had excellent base stability. N-1-(4-Nitro-1,3-dioxoindan-2-ylidene)-ethyl (Nde; Kellam, 1996; Mosher and Meier, 1970) protection of amino acids gave similar vinylogous systems, and deprotection of these could be achieved in very mild conditions.

For many years chemists have attempted to transpose the solid-phase methodology which is routinely used for peptide synthesis to oligosaccharide synthesis, with varying degrees of success. The first attempt was approximately 25 years ago (Frechet and Schuerch, 1971; Frechez and Schuerch, 1972; Guthrie et al, 1971; Guthrie et al, 1973). However, the ozone-mediated deprotection product was an aldehyde-substituted glycoside. Danishefsky and coworkers described the solid phase synthesis of the Lewis b Antigen (Randolph et al, 1995) and N-linked glycopeptides (Roberge et al, 1995) by initial attachment of the primary sugar unit of the oligosaccharide to a 1% divinylbenzene-styrene co-polymer support via a silyl ether linkage. The resin-bound sugar moiety was in this instance a glycal, with on-resin activation achieved via epoxidation of the double bond, and the resulting glycal residue acting as a sugar donor through nucleophile ring-opening of the epoxide. Since there are no colorimetric methods available to the sugar chemist to monitor on-resin glycosylations, the only means of assessing the progress of the reaction is by lysis of the oligosaccharide-resin bond and subsequent analysis of the cleavage product, usually by thin layer chromatography. The tetra-n-butylammonium fluoride-mediated deprotection conditions required to cleave Danishefsky's silyl ether linker are both hazardous and slow. This, coupled with the requirement for on-resin activation of the tethered glycals, makes the overall strategy and methodology far from ideal.

In an alternative approach, Douglas and coworkers described the synthesis of D-mannopentose using a polyethyleneglycol w-monomethylether co-polymer and a succinoyl or an α,α'-dioxyxylyl diether linker (Douglas et al, 1995). The reactions were carried out in solution phase, with removal of unused reactants being achieved by precipitation of the oligosaccharide-polymer complex and subsequent washing. In the latter example, cleavage of the oligosaccharide-polymer bond was achieved through catalytic hydrogenation, which required exposure of the conjugate to 1 atm of $H_2$ for 48 h to achieve respectable yields. This again is far too slow to allow effective monitoring of individual glycosylation reactions. Yan et al reported sulphoxide-mediated glycosylation on a Merrifield resin, using a thiophenol linker for the attachment of the primary sugar residue (Yan et al, 1994). This method resulted in the construction of (1–6)-linked oligosaccharides, and was suitable for synthesis of both α- and β-glycosidic linkages. However, the thioglycosidic linkage to the resin dictates that similar sugar donors cannot be employed in this strategy.

Recently Rademann and Schmidt reported the use of trichloroacetimidate sugar donors to a resin bound sugar tethered via an alkyl thiol (Rademann and Schmidt, 1996); once again, however, this method precludes the use of the far superior thioglycoside sugar donors. Meanwhile, Adinolfi et al described the synthesis of disaccharides using a polyethyleneglycol-polystyrene resin, with connection of the first sugar to the polymeric support through a succinate spacer (Adinolfi et al, 1996). However, the acid lability displayed by this linker means that the primary sugar cannot be linked to the resin via the glycosidic position.

These examples illustrate that the critical element in solid phase synthesis is the nature of the linker between the solid support and the initial synthon. The linker must display excellent stability to the conditions of coupling and deprotection, yet in the case of solid phase oligosaccharide synthesis, it should also be rapidly and efficiently cleaved to allow monitoring of the progress of individual coupling reactions. The cleavage should ideally be achieved by the use of a relatively innocuous chemical reagent. There remains a need in the art for simple, efficient and economical methods for solid-phase synthesis of oligosaccharides.

In our allowed U.S. Pat. No. 6,523,337, which is the U.S. national stage application of International Patent Application No. PCT/AU97/00544 (priority date Aug. 28, 1996), we have shown several ways of immobilizing 2-acyl-5,5-dimethyl-1,3-cyclohexanedione and of utilizing the immobilized compound in solid phase oligosaccharide synthesis. In our U.S. Pat. No. 6,462,183, which is the U.S. national stage application of International Patent Application No. PCT/AU98/00131 (priority date Feb. 28, 1997), we have shown that vinylogous amide protection of amino sugars could be achieved in simple reactions using Dde-OH and Nde-OH reagents. The Dde- and Nde-protected monosaccharides survived most of the hydroxyl protective group manipulations and the reactions which occurred at the glycosidic center, affording a wide variety of sugar donors. These vinylogous amide-protected aminosugar donors were not neighbouring group active carbohydrates, giving anomeric mixtures of glycosides during the glycosylations. We have demonstrated the stability and the ease of deprotection of the Dde- and Nde-protected aminosugars in carbohydrate-based methodology.

Unfortunately even these protective strategies still present some difficulties.

The Dde-protected aminosugars are not stable in the presence of sodium cyanoborohydride and metal hydrides. These reagents are often used in benzylidene ring opening reactions and during benzyl protection of hydroxyl groups.

This hydride sensitivity of the Dde group limits its application in carbohydrate chemistry. The preparation of 2-acyldimedones is very often difficult. One of the major side reactions is O-acylation, which lowers the overall yields and causes difficult chromatographic purification problems.

Nde-protection of primary amines always gives a mixture of E/Z isomers which may not be separable, causing difficult characterisation problems. The formation of 2-acetyl-4-nitroindan-1,3-dione involves the reaction between 4-nitrophthalic anhydride and 2,4-pentanedione via a condensation and two rearrangements. This synthetic strategy does not give an opportunity to prepare Nde-OH analogues.

We have now synthesized a family of novel compounds useful as protecting and linking groups for organic synthesis.

SUMMARY OF THE INVENTION

In its most general aspect, the invention provides a cyclic compound of general formula I

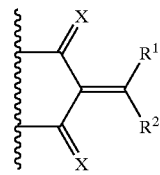

I wherein the ring is a cycloalkyl, substituted cycloalkyl, cycloheteroalkyl, substituted cycloheteroalkyl, saturated bicyclo[p, q, r], substituted saturated bicyclo[p, q, r], saturated heterobicyclo[p, q, r], substituted saturated heterobicyclo[p, q, r], unsaturated bicyclo[p, q, r], substituted unsaturated bicyclo[p, q, r], unsaturated heterobicyclo [p, q, r], substituted unsaturated heterobicyclo[p, q, r], saturated tricyclo[p, q, r, s], substituted saturated tricyclo[p, q, r, s,], unsaturated tricycloalkyl[p, q, r, s] unsaturated substituted tricycloalkyl[p, q, r, s], saturated heterotricyclo [p, q, r, s,], substituted saturated heterotricyclo[p, q, r, s,], unsaturated heterotricyclo[p, q, r, s,] or substituted unsaturated heterotricyclo[p, q, r, s,] ring system; where p, q, r and s may be the same or different, and each of p, q, r and s is an integer of from 0 to 5;

X is oxygen, sulphur, imino or substituted imino;

$R^1$ is hydrogen; an alkyl, alkenyl, alkynyl, heteroalkyl, aryl, heteroaryl, cycloheteroaryl, cycloalkyl, heterocycloalkyl, alkanal, or thioalkanal group, each of which may be substituted or unsubstituted; $NH_2$, guanidino, CN, substituted amino, quaternary ammonium, $O^-$, formyl, imino or substituted imino, COOH, or a carboxylic acid derivative;

$R^2$ is an alkylamino, dialkylamino, arylamino, or diarylamino group, each of which may be substituted or unsubstituted; O-substituted hydroxylamino, substituted or unsubstituted hydrazino, substituted or unsubstituted hydrazido, substituted or unsubstituted thiohydrazido, semicarbazido, thiosemicarbazido, OH, $O^-M, NH_2$, NHOH, SH, $S^-M^+$, halogen; O-alkyl, O-acyl, O-aryl, alkylthio, S-aryl, acylthio, alkylsulfonyl or arylsulfonyl, each of which may be substituted or unsubstituted; and M is a metal ion, or an organic or inorganic cation such as a quaternary amine group, a trityl group or an ammonium group, with the provisos that the compound is not one disclosed in our U.S. Pat. No. 6,573,337 which is the U.S. national stage application of International Patent Application No. PCT/AU97/00544.

A wide variety of suitable cations is known in the art. The metal ion can be mono- or multivalent, and may form a complex salt.

Preferably the ring is 4- to 8-membered cycloalkyl, substituted cycloalkyl, cycloheteroalkyl or substituted cycloheteroalkyl.

Alternatively in other preferred forms, the ring is a 5- to 8-membered ring of the lactone or lactam type, or a 6- to 8-membered ring of the carbamido or substituted carbamido type, as follows:

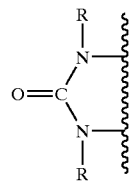

in which each R is independently H, substituted or unsubstituted alkyl, aryl, alkenyl, alkynyl or acyl, or may be a 6- to 8-membered ring of the carbonate type, as follows:

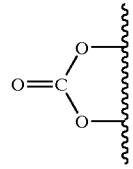

It will be clearly understood that in the general formulae of this specification, each of the substituent groups R, $R^1$, $R^2$ and $R^3$ may itself be substituted, ie. one or more hydrogen atoms may be replaced by a substituent group.

For the purposes of this specification the term "substituted" in the definitions of R, $R^1$ and $R^2$, and in definitions of other substituents within this specification, means that the substituent is itself substituted with a group which modifies the general chemical characteristics of the chain. Preferred substituents include but are not limited to halogen, nitro, amino, azido, oxo, hydroxyl, thiol, carboxy, carboxy ester, carboxyamide, alkylamino, alkyldithio, alkylthio, alkoxy, acylamido, acyloxy, or acylthio, each of 1 to 3 carbon atoms. Such substituents can be used to modify characteristics of the molecule as a whole, such as stability, solubility, and ability to form crystals. The person skilled in the art will be aware of other suitable substituents of similar size and charge characteristics which could be used as alternatives in a given situation.

In one group of preferred embodiments, the compound is of general formula II

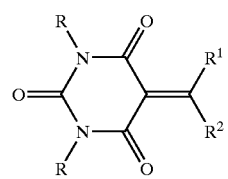

II in which each R is independently H or a substituted or unsubstituted alkyl, aryl, cycloalkyl, heteroalkyl, heteroaryl or heterocycloalkyl; and $R^1$ and $R^2$ are as defined in general formula I.

Preferably each R has 1 to 6, more preferably 1 to 4 carbon atoms.

In another group of preferred embodiments, the compound is of general formula III

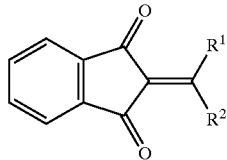

III in which
R¹ and R² are as defined in general formula I.

The compounds of the invention are useful in a wide variety of areas of organic chemistry. The compounds are especially useful in the solution and/or solid phase synthesis of oligosaccharides and peptides. Uses of the compounds of the invention thus include but are not limited to the following:

1. Linker groups for solid-phase oligosaccharide synthesis;
2. N-protecting groups for protection of amino sugars in oligosaccharide synthesis;
3. Linker groups for solid phase organic synthesis;
4. N-protecting groups for organic synthesis;
5. N-side chain and/or $N_\alpha$ protecting groups for solid or solution phase peptide synthesis;
6. Amino protecting groups for sugars, peptides and organic compounds, affording an additional free enamine;
7. Certain compounds of the invention are chiral; these are useful in resolution or enantiomers and in stereospecific synthesis.
8. Linker groups for coupling of a starter group to a resin or solid phase synthesis of oligosaccharides, peptides and other organic compounds.

Thus in a second aspect, the invention provides an N-protecting group for oligosaccharides, amino acids, peptides or organic compounds.

An example of the application of this group for the protection of amino groups during oligosaccharide synthesis is shown in general formula IV

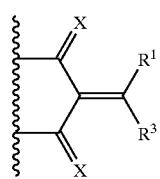

IV wherein the ring, X and R¹ are as defined in general formula I, and

R³ is a protected, unprotected or substituted sugar amino-, a glycosylamino-, or a glycosylamino group of an oligosaccharide; or a mono- or oligosaccharide coupled through a substituted or unsubstituted alkylamino-, arylamino-, cycloalkylamino, heteroalkylamino, heteroarylamino or heterocycloalkylamino group.

In one group of preferred embodiments, the compound is of general formula V

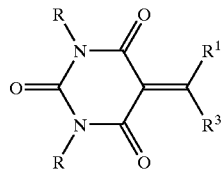

V in which R and R¹ are as defined in general formula II, and R³ is as defined in general formula IV.

Preferably R³ is a protected, unprotected or substituted sugar amino-, a glycosylamino-, or a glycosylamino group of an oligosaccharide.

Alternatively, R³ is an oligosaccharide-O—CH₂—(C₆H₄)—NH—, monosaccharide-O—CH₂—(C₆H₄)—NH—, oligosaccharide-CO₂CH₂—(C₆H₄)NH—, or monosaccharide-CO₂CH₂—(C₆H₄)—NH group.

In a third aspect the invention provides a support of general formula VI for solid-phase synthesis of oligosaccharides, peptides or organic compounds, comprising a resin and a linker covalently attached to the resin:

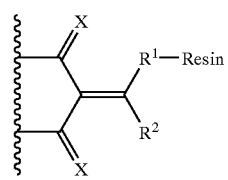

VI wherein the ring, X and R² are as defined in general formula I, and

R¹ is a substituted or unsubstituted alkyl, cycloalkyl, heteroalkyl, heteroaryl, heterocycloalkyl or carboxylamido spacer group which is directly coupled to the resin support, or which may optionally be coupled to the resin support via a suitable covalent linkage, which is stable to conditions of oligosaccharide synthesis and cleavage.

The covalent linkage may suitably be provided by a —CONH—, —O—, —S—, —NH—, —COO—, —COS—, —CH=N—, —NHCONH—, —NHCSNH, —NHNH— grouping, eg. Spacer-CONH-resin, Spacer-O-resin, Spacer-S-resin, Spacer-S-S-resin, Spacer-CO₂-resin, Spacer-CH=N-resin, Spacer-NHCONH-resin, Spacer-NHCSNH-resin, Spacer-NHNH-resin. Other possible covalent linking groups will be known to those skilled in the art.

In a particularly preferred embodiment, the linker is a barbituric acid of general formula VII

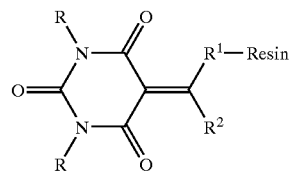

VII in which R and R² are as defined in general formula I, and
R¹ is as defined in general formula VI,
in which a compound of general formula II is directly coupled to the resin support, or may optionally be coupled to the resin support via a suitable covalent linkage which is stable to conditions of oligosaccharide synthesis and cleavage.

The covalent linkage may suitably be provided by a —CONH—, —O—, —S—, —NH—, —COO—, —COS—, —CH=N—, —NHCONH—, —NHCSNH, or —NHNH— grouping, eg. Spacer-CONH-resin, Spacer-O-resin, Spacer-S-resin, Spacer-S-S-resin, Spacer-CO$_2$-resin, Spacer-CH=N-resin, Spacer-NHCONH-resin, Spacer-NHCSNH-resin, Spacer-NHNH-resin. Other possible covalent linking groups will be known to those skilled in the art.

The resin may be any resin which swells in water and/or in an organic solvent, and which comprises one of the following substituents: halogen, hydroxy, carboxyl, SH, NH$_2$, formyl, SO$_2$NH$_2$, or NHNH$_2$, for example methylbenzhydrylamine (MBHA) resin, amino or carboxy tentagel resins, or 4-sulphamylbenzyl AM resin. Other suitable resins will be known to those skilled in the art. Alternatively, supports such as controlled-pore glass or soluble polymer supports may be used. These are well known in the art.

The invention also provides a method of solid-phase synthesis of oligosaccharides, comprising the step of sequentially linking mono- or oligosaccharide groups to a support as described above.

The linker may be synthesised directly on the resin in a stepwise manner prior to the coupling of the initial sugar group, or the linker-initial sugar conjugate may be synthesised in solution phase and subsequently coupled to the solid support, with subsequent sugars being sequentially attached. Preferably the second and all subsequent sugar groups are coupled to the oligosaccharide chain-resin conjugate after the last sugar in the oligosaccharide chain is partially deprotected.

The first sugars attached to the resin-linker unit may be unprotected, partially protected or fully protected glycosides, aminoglycosides, or ether- or amino-linked sugars.

Preferably the first sugar coupled to the resin is an aminosugar, an aminoglycoside or an amino-oligosaccharide, or a glycosyl amines of an oligosaccharide.

In one particularly preferred embodiment the support comprises a resin, a linker and a saccharide selected from the group consisting of monosaccharide, oligosaccharides, or aminosaccharides and aminooligosaccharides.

The building block mono- or oligosaccharide-donors may be any activated sugar, including but not limited to orthoesters, thio-orthoesters, cyanoalkylidene derivatives, 1-O-acyl sugars, amino sugars, acetimidates, trichloroacetimidates, thioglycosides, aminoglycosides, aminoligosaccharides, glycosylamines of oligosaccharides, glycosyl thiocyanates, pentenyl glycosides, pentenoylglycosides, isopropenyl glycosides, glycals, tetramethylphosphoro diamidates, sugar diazirines, selenoglycosides, phosphorodithioates, glycosyldialkylphosphites, glycosylsulphoxides and glycosylfluorides.

Preferably partial sugar deprotection is achieved by using acyl-type, trityl, methoxytrityl, methoxybenzyl, various silyl and/or photolabile protecting groups in addition to permanent ether-type protecting groups. This permits the synthesis of branched oligosaccharides by using two orthogonal hydroxy-protecting groups on a single sugar donor.

The synthesised oligosaccharide can be cleaved from the resin using ammonia, hydrazine or a primary amine, such as butylamine or cyclohexylamine. For the preparation of aminoglycosides, ammonia or a suitable primary amine in an organic solvent is preferably employed. For the preparation of hydrazides, hydrazine in water or an organic solvent is preferably employed. For the preparation of oligosaccharides, ammonia in water or organic solvent is preferably employed, followed by acidification. When the linker contains a 4-aminobenzyl moiety, after cleavage as described above the first sugar is released still protected by the aminobenzyl group; this can be removed by hydrogenation if desired.

In a preferred embodiment, the invention provides a reagent for solution phase synthesis of sugar-containing compounds, comprising a barbituric acid derivative compound of general formula II as defined above.

The compounds of the invention are suitable for use as protective groups in methods of solid phase oligosaccharide synthesis, in which sugar units are linked to a resin. Any suitable linker compound may be used, including compounds of the invention. It is contemplated that linkers and methods described in our U.S. Pat. No. 6,573,337 which is the U.S. national stage application of International Patent Application No. PCT/AU97/00544, are also suitable for use with the compounds of this invention.

Thus in a fourth aspect the invention provides a linker-saccharide complex, comprising a linker group and a starting compound comprising a protecting group of general formula I or II as defined above. Any suitable linker compound may be used, including compounds of the invention. Again, it is contemplated that linkers and methods described in our U.S. Pat. No. 6,537,332, which is the U.S. national stage application of International Patent Application No. PCT/AU97/00544, may be used.

In a fifth aspect the invention provides a method of solution phase synthesis of oligosaccharides, comprising the step of sequentially linking mono- or oligosaccharide groups to a linker-saccharide complex as described above.

These methods are particularly useful for combinatorial synthetic applications. The solution phase method of the invention may, for example, be used for combinatorial synthesis of aminoglycoside compounds.

The invention also provides kits useful in solution phase synthesis or combinatorial synthesis of oligosaccharides or peptides, comprising either a) a resin-linker-saccharide or resin-linker-peptide (or amino acid) support, b) a linker-saccharide or linker-peptide (or amino acid) complex, or c) a resin-linker support, according to the invention, as described above.

For peptide synthesis it may be convenient in some circumstances to start with a resin-linker-amino acid support or linker-amino acid complex, while in others a starter peptide may more suitably be provided in the support or linker complex. The kit may optionally also comprise one or more further reagents such as protecting agents, deprotecting agents, and/or solvents suitable for solid phase or combinatorial synthesis. The person skilled in the art will be aware of suitable further reagents. Different types of kit can then be chosen according to the desired use.

The invention also provides a kit useful in solid phase synthesis or combinatorial synthesis of oligosaccharides, comprising a linker-saccharide complex according to the invention, as described above. The kit may optionally also comprise one or more further reagents such as protecting agents, deprotecting agents, and/or solvents suitable for solid phase or combinatorial synthesis. The person skilled in the art will be aware of suitable further reagents. Different types of kit can then be chosen according to the desired use.

For the purposes of this specification it will be clearly understood that the word "comprising" means "including but not limited to", and that the word "comprises" has a corresponding meaning.

DETAILED DESCRIPTION OF THE INVENTION

Abbreviations used herein are as follows:

| | |
|---|---|
| Ac | Acetyl |
| AcOH | Acetic acid |
| ADA | 5-Acyl-1,3-dimethylbarbituric acid |
| Alloc | Allyloxycarbonyl |
| Boc | tert-Butoxycarbonyl |
| Bu | butyl |
| Cbz | Benzyloxycarbonyl |
| DBU | 1,8-Diazabicyclo[5.4.0]undec-7-ene |
| DCC | N,N'-Dicyclohexylcarbodiimide |
| Dde | N-1-(4,4-Dimethyl-2,6-dioxocyclohexylidene)-ethyl |
| DMAP | 4-Dimethylaminopyridine |
| Dmc | N-(4,4-Dimethyl-2,6-dioxocyclohexylidene-methylene) |
| DMF | N,N'-Dimethylformamide |
| EtOH | Ethanol |
| FAB MS | Fast atom bombartment mass spectrometry |
| Fmoc | 9-Fluorenylmethoxycarbonyl |
| MBHA | methylbenzylhydramine |
| Me | Methyl |
| MeOH | Methanol |
| Nde | 1-(4-Nitro-1,3-dioxoindan-2-ylidene)ethyl |
| NMR | Nuclear magnetic resonance |
| ODmab | -{N-[1-(4,4-dimethyl-2,6-dioxocyclohexyl-idene)-3-methylbutyl]-amino}benzyl alcohol |
| PhFl | 9-Phenylfluorenyl |
| TBAF | Tetrabutylammonium fluoride |
| TEAB | Tetraethylammonium bromide |
| Teoc | 2-(Trimethylsilyl)ethoxycarbonyl |
| TNBS | 2,4,6-trinitrobenzene sulphonic acid |
| Troc | 2,2,2-Trichloroethoxycarbonyl |

The invention will now be described in detail by way of reference only to the following non-limiting examples, in which the structures of individual compounds are as summarised in the following tables and structures.

TABLE 1

Compounds 1–20

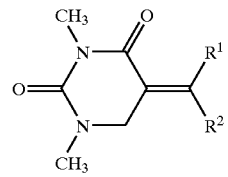

| Compound | $R^1$ | $R^2$ |
|---|---|---|
| 1 | OH | $CH_3$ |
| 2 | NHBu | $CH_3$ |
| 3 | OH | Ph |
| 4 | NHBu | Ph |
| 5 | OH | 9-fluorenyl |
| 6 | OH | $CH_2Cl$ |
| 7 | OH | $CHCl_2$ |
| 8 | OH | Bn |
| 9 | OH | $CHPh_2$ |
| 10 | OH | $-(CH_2)_3COOH$ |
| 11 | OH | t-BU |
| 12 | OH | 1-adamantyl |
| 13 | $NH_2$ | $CCl_3$ |
| 14 | $-NHCH_2COOH$ | $CH_3$ |
| 15 | $-NHCH_2COOH$ | Ph |
| 16 | $-NHCH_2COOH$ | Bn |
| 17 | $-NHOH$ | Ph |
| 18 | $-NHNHCOCH_3$ | Ph |

TABLE 1-continued

Compounds 1–20

| Compound | $R^1$ | $R^2$ |
|---|---|---|
| 19 | $-NH-NH_2$ | Ph |
| 20 | $NH_2$ | Ph |

TABLE 2

Compounds 21–29

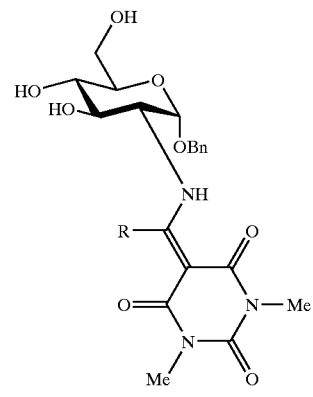

| Compound | R |
|---|---|
| 21 | $CH_3$ |
| 22 | Ph |
| 23 | 9-fluorenyl |
| 24 | Bn |
| 25 | $CHPh_2$ |
| 26 | $-(CH_2)_3COOH$ |
| 27 | $NH_2$ |
| 28 | t-Bu |
| 29 | 1-adamantyl |

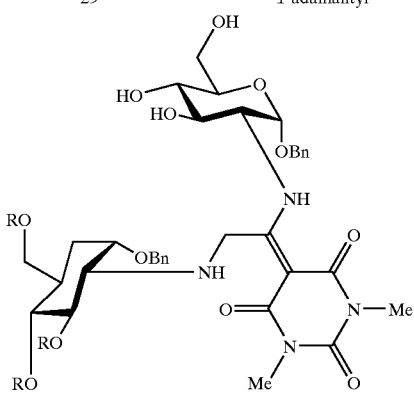

30

TABLE 2-continued

Compounds 21–29

| Compound | R |
|---|---|
| 31 | (structure shown) |
| 32 | R = Ac |
| 37 | R = H |
| 33 | (structure shown) |
| 34 | (structure shown) |
| 35 | R = NH$_2$ |
| 36 | R = OH |
| 38 | (structure shown) |
| 39 | (structure shown) |

We have now developed a novel enamine-type protective system, including the preparation of reagents, and methods for selective amino group protection and deprotection. This has been illustrated by synthesizing a number of 5-acyl-1,3-dimethyl-barbituric acids (ADA) (Examples 1–11). During the syntheses only C-acyl products were formed; no O-acylation was observed. The 5-acylation of 1,3-dimethylbarbituric acid was successfully carried out using carboxylic acids in the presence of DCC and DMAP (Examples 5 to 9). The more reactive acyl chlorides (Examples 3 to 4) and anhydrides (Examples 1 to 2) were also used, giving the same products in a DMAP-catalyzed reaction. Trichloroacetonitrile was used to construct a similar structure in the present of DBU (Example 10).

The 5-acyl-1,3-dimethylbarbituric acids were easily crystallized from polar solvents, avoiding the need for chromatographic purifications. These reagents are very cheap and easy to synthesize in a single reaction from the readily available 1,3-dimethyl-barbituric acid. We have used the 5-acyl-1,3-dimethylbarbituric acid reagents to prepare a wide variety of protected primary alkylamines (Examples 12–13), aminosugars (Examples 22 to 28) and amino acids (Examples 14 to 16).

The ADA-protected aminosugars can be used as aminosugar acceptors and aminosugar donors for solid or solution phase oligosaccharide synthesis. The ADA-protected amino acids are particularly useful as reagents for solid-phase peptide and glycopeptide syntheses, because they are unable to form oxazolones during the coupling reactions. Thus, no racemization can occur during the peptide bond formation (racemization can only occur in base-catalyzed proton abstraction). The ADA-protection is ideally orthogonal to the Boc-protection and quasi-orthogonal to the Fmoc system.

We have demonstrated that the system can be used for the protection of hydroxylamines (Example 17), hydrazines (Example 19) and hydrazides (Example 18). The vinylogous amide protection of amino groups was efficiently achieved by simply refluxing the unprotected amines with the precursor (5-acyl-1,3-dimethylbarbituric acid) in abs EtOH.

The ADA-protected derivatives are very stable in a wide range of reactions and work-up conditions. Different reagents ($NH_3$, $N_2H_4$, $NH_2OH$, n—$BuNH_2$, $BnNH_2$, NH—$NHCOCH_3$, $N_2H_4$x$AcOH$, NaOH) have been developed for the cleavage of the protecting groups (Examples 17 to 20). The speed of protection and cleavage depends on the electronic and steric effects of the 5-acyl functional group.

We have also synthesized bifunctional 5-acyl-1,3-dimethylbarbituric acids (Example 11), which can be used as linkers for solid phase organic chemistry. We have successfully immobilized a bifunctional 5-acyl-1,3-dimethylbarbituric acid producing a "resin-linker conjugate" (Example 35). We have proved that this "resin-linker conjugate" was suitable for solid phase oligosaccharide synthesis by immobilizing a monosaccharide (Example 32), deprotecting its hydroxyl groups (Example 33) and later realising it during the cleavage (Example 33). We have demonstrated that the resin-linker conjugate was reusable, regenerating the original hydroxyl function with aqueous base treatment (Example 36). Alternatively the "amino-substituted resin-linker conjugate" itself may be used for the next immobilization (Example 34).

The introduction of another reactive centre into the protecting group makes the system more flexible. Using 5-chloroacetyl-1,3-dimethylbarbituric acid, we have synthesised a chiral carbohydrate containing reagent (Example 31) for protection of organic compounds bearing an amino functionality. These types of molecules are especially suitable for resolution of enantiomers.

The 5-trichloroacetimino-1,3-dimethyl-barbituric acid gave rare 1,1-elimination in the reaction with primary amines, affording a novel type of compound (Example 29).

EXAMPLE 1

5-Acetyl-1,3-Dimethyl-2,4,6(1H,3H,5H)-Pyrimidinetrione (Dtpc-OH) 1

A mixture of 1,3-dimethylbarbituric acid (10 g, 64.04 mmol), 4-dimethylaminopyridine (9.49 g, 158.0 mmol) in dry $CH_2Cl_2$ (190 ml) was cooled to 0° C. and acetic anhydride (7.35 ml, 77.9 mmol) added dropwise in 15 min. The reaction mixture was stirred overnight at room temperature, diluted with $CH_2Cl_2$ (500 ml) and washed with 2 N HCl solution (80 ml). The organic phase was dried over $MgSO_4$ and evaporated. The residue was crystallised from MeOH, giving 5-acetyl-1,3-dimethyl-2,4,6(1H,3H,5H)-pyrimidinetrione 1 (8.6 g, 68%).

$R_f$ 0.37 (EtOAc/hexane 2:1);

FAB MS $C_8H_{10}N_2O_4$ (198.18) m/z (%) 199 $[M+H]^+$ (100), 183 (18).

$^1$H NMR ($CDCl_3$) d 17.26 (s, 1H, OH), 3.36, 3.32 (2s, 6H, 2 $NCH_3$), 2.71 (s, 3H, $CH_3$).

EXAMPLE 2

5-Chloroacetyl-1,3-Dimethyl-2,4,5(1H,3H,5H)-Pyrimidinetrione (Dtpc-OH) 6

A mixture of 1,3-dimethylbarbituric acid (5.00 g, 32.02 mmol), 4-dimethylaminopyridine (9.76 g, 80.05 mmol) in dry $CH_2Cl_2$ (75 ml) was cooled to 0° C. and chloroacetic anhydride (6.57 g, 38.46 mmol) added. The reaction mixture was stirred at room temperature overnight, diluted with $CH_2Cl_2$ (150 ml) and washed with 2 N HCl solution (40 ml). The organic phase was dried over $MgSO_4$ and evaporated. The residue was crystallised from MeOH, giving 5-chloroacetyl-1,3-dimethyl-2,4,6(1H,3H,5H)-pyrimidinetrione 6 (4.57 g, 61%).

$R_f$ 0.41 (hexane/EtOAc/AcOH 10:5:0.1);

FAB MS $C_8H_9ClN_2O_4$ (232.62) m/z (%) 233 $[M+H]^+$ (100), 197 (58), 183 (15).

$^1$H NMR ($CDCl_3$) d 17.93 (s, 1H, OH), 4.97 (s, 2H, $CH_2$), 3.41, 3.34 (2s, 6H, 2 $NCH_3$).

EXAMPLE 3

5-Benzoyl-1,3-Dimethyl-2,4,6(1H,3H,5H)-Pyrimidinetrione (Dtpb-OH) 3

A mixture of 1,3-dimethylbarbituric acid (5 g, 32.02 mmol), 4-dimethylaminopyridine (4.74 g, 38.79 mmol) in dry $CH_2Cl_2$ (75 ml) was cooled to 0° C. and benzoyl chloride (4.95 g, 35.22 mmol) added dropwise in 15 min. The reaction mixture was stirred for 3 h at room temperature, diluted with $CH_2Cl_2$ (150 ml) and washed with 2 N HCl solution (40 ml). The organic phase was dried over $MgSO_4$ and evaporated. The residue was crystallised from diisopropylether then recrystallised from MeOH, giving 5-benzoyl-1,3-dimethyl-2,4,6(1H,3H,5H)-pyrimidinetrione 3 (5.32 g, 64%).

$R_f$ 0.45 (EtOAc/hexane/TFA 10:15:0.1);

FAB MS $C_{13}H_{12}N_2O_4$ (260.25) m/z (%) 283 $[M+Na]^+$ (25), 261 $[M+H]^+$ (100), 245 (45), 183 (55).

$^1$H NMR ($CDCl_3$) d 16.58 (s, 1H, OH), 7.57–7.45 (m, 5H, 5 Ar—H), 3.44, 3.27 (2s, 6H, 2 $NCH_3$).

EXAMPLE 4

5-Pivaloyl-1,3-dimethyl-2,4,6(1H,3H,5H)-pyrimidinetrione (Dtppe-OH) 11

A mixture of 1,3-dimethylbarbituric acid (5 g, 32.02 mmol), 4-dimethylaminopyridine (4.69 g, 38.42 mmol) in dry $CH_2Cl_2$ (75 ml) was cooled to 0° C. and pivaloyl chloride (4.24 g, 35.22 mmol) added dropwise in 15 min. The reaction mixture was stirred at room temperature overnight, diluted with $CH_2Cl_2$ (150 ml) and washed with 2 N HCl solution (40 ml). The organic phase was dried over $MgSO_4$ and evaporated. The residue was purified by chromatography using hexane/EtOAc/AcOH 15:5:0.1 as the mobile phase to give 5-pivaloyl-1,3-dimethyl-2,4,6(1H,3H,5H)-pyrimidinetrione 11 (5.46 g, 71%).

$R_f$ 0.65 (hexane/EtOAc/AcOH 15:5:0.1);

FAB MS $C_{11}H_{16}N_2O_4$ (240.26) m/z (%) 263 [M+Na]$^+$ (7), 241 [M+H]$^+$ (100), 223 (15), 183 (15).

$^1$H NMR (CDCl$_3$) d 19.14 (s, 1H, OH), 3.38, 3.33 (2s, 6H, 2 NCH$_3$), 1.41 (s, 9H, 3 CH$_3$).

EXAMPLE 5

5-(9-Fluorenylcarbonyl)-1,3-Dimethyl-2,4,6(1H,3H,5H)-Pyrimidinetrione (Dtpf-OH) 5

A mixture of 1,3-dimethylbarbituric acid (2.5 g, 16.01 mmol), 9-fluorenylcarboxylic acid (5.05 g, 24.01 mmol), 4-dimethylaminopyridine (0.98 g, 8.00 mmol) in dry $CH_2Cl_2$ (15 ml) was cooled to 0° C. and 1,3-dicyclohexylcarbodiimide (3.30 g, 16.01 mmol) added. The reaction mixture was stirred at room temperature overnight and filtered. The solid was washed with $CH_2Cl_2$ (50 ml) and the combined solution was washed with 2 N HCl solution (5 ml). The organic phase was dried over $MgSO_4$ and evaporated. The residue was crystallised from recrystallised from MeOH giving 5-(9-fluorenyl-carbonyl)-1,3-dimethyl-2,4,6(1H,3H,5H)-pyrimidinetrione 5 (2.85 g, 69%).

$R_f$ 0.49 (EtOAc/hexane/TFA 10:25:0.1);

FAB MS $C_{20}H_{16}N_2O_4$ (348.35) m/z (%) 349 [M+H]$^+$ (100), 338 (32), 183 (72), 164 (71).

$^1$NMR (CDCl$_3$) d 17.33 (s, 1H, OH), 7.81 (d, 2H, 2 Ar—H), 7.42 (m, 4H, 4 Ar—H), 7.30 (d, 2H, 2 Ar—H), 6.92 (s, 1H, CH), 3.48, 3.40 (2s, 6H, 2 NCH$_3$).

EXAMPLE 6

5-Dichloroacetyl-1,3-Dimethyl-2,4,6(1H,3H,5H)-Pyrimidinetrione (Dtpd-OH) 7

A mixture of 1,3-dimethylbarbituric acid (5.00 g, 32.05 mmol), dichloroacetic acid (6.19 g, 48.03 mmol), 4-dimethylaminopyridine (1.95 g, 16.01 mmol) in dry $CH_2Cl_2$ (30 ml) was cooled to 0° C. and 1,3-dicyclohexylcarbodiimide (7.26 g, 35.22 mmol) added. The reaction mixture was stirred at room temperature overnight and filtered. The solid was washed with $CH_2Cl_2$ (150 ml) and the combined solution was washed with 2 N HCl solution (40 ml). The organic phase was dried over $MgSO_4$ and evaporated. The residue was crystallised from MeOH giving 5-dichloroacetyl-1,3-dimethyl-2,4,6(1H,3H,5H)-pyrimidinetrione 7 (5.41 g, 63%).

$R_f$ 0.27 (hexane/EtOAc/AcOH 10:5:0.1);

FAB MS $C_8H_8Cl_2N_2O_4$ (267.07) m/z (%) 289 [M+Na]$^+$ (10), 267[M+H]$^+$ (100), 231 (66), 197 (33), 183 (24).

$^1$H NMR (CDCl$_3$) d 17.94 (s, 1H, OH), 7.91 (s, 1H, CH), 3.43, 3.35 (2s, 6H, 2 NCH$_3$).

EXAMPLE 7

5-Phenylacetyl-1,3-Dimethyl-2,4,6(1H,3H,5H)-Pyrimidinetrione (Dtpp-OH) 8

A mixture of 1,3-dimethylbarbituric acid (5.00 g, 32.05 mmol), phenylacetic acid (6.53 g, 48.03 mmol), 4-dimethylaminopyridine (1.95 g, 16.01 mmol) in dry $CH_2Cl_2$ (30 ml) was cooled to 0° C. and 1,3-dicyclohexylcarbodiimide (7.26 g, 35.22 mmol) added. The reaction mixture was stirred at room temperature overnight and filtered. The solid was washed with $CH_2Cl_2$ (150 ml) and the combined solution was washed with 2 N HCl solution (40 ml). The organic phase was dried over $MgSO_4$ and evaporated. The residue was crystallized from MeOH giving 5-phenylacetyl-1,3-dimethyl-2,4,6(1H,3H,5H)-pyrimidinetrione 8 (6.10 g, 69%).

$R_f$ 0.41 (hexane/EtOAc/AcOH 10:5:0.1);

FAB MS $C_{14}H_{14}N_2O_4$ (274.27) m/z (%) 297 [M+Na]$^+$ (11), 275 [M+H]$^+$ (100), 257 (13), 183 (31).

$^1$H NMR (CDCl$_3$) d 17.61 (s, 1H, OH), 7.54–7.26 (m, 5H, 5 Ar—H), 4.49 (s, 2H, CH$_2$Ar), 3.38, 3.34 (2s, 6H, 2 NCH$_3$).

EXAMPLE 8

5-Diphenylacetyl-1,3-dimethyl-2,4,6(1H,3H,5H)-pyrimidinetrione (Dtpd-OH) 9

A mixture of 1,3-dimethylbarbituric acid (5.00 g, 32.05 mmol), diphenylacetic acid (10.19 g, 48.03 mmol), 4-dimethylaminopyridine (1.95 g, 16.01 mmol) in dry $CH_2Cl_2$ (30 ml) was cooled to 0° C. and 1,3-dicyclohexylcarbodiimide (7:26 g, 35.22 mmol) added. The reaction mixture was stirred at room temperature overnight and filtered. The solid was washed with $CH_2Cl_2$ (150 ml) and the combined solution was washed with 2 N HCl solution (40 ml). The organic phase was dried over $MgSO_4$ and evaporated. The residue was crystallized from EtOH giving 5-diphenylacetyl-1,3-dimethyl-2,4,6(1H,3H,5H)-pyrimidinetrione 9 (6.70 g, 59%).

$R_f$ 0.64 (hexane/EtOAc/AcOH 10:5:0.1);

FAB MS $C_{20}H_{18}N_2O_4$ (350.36) m/z (%) 373 [M+Na]$^+$ (8), 351 [M+H]$^+$ (100), 338 (24), 333 (16).

$^1$H NMR (CDCl$_3$) d 18.28 (s, 1H, OH), 7.32–7.27 (m, 10H, 10 Ar—H), 7.02 (s, 1H, CHAr$_2$), 3.36, 3.31 (2s, 6H, 2 NCH$_3$).

EXAMPLE 9

5-(1-Adamantanecarbonyl)-1,3-Dimethyl-2,4,6(1H,3H,5H)-Pyrimidinetrione (Dtpa-OH) 12

A mixture of 1,3-dimethylbarbituric acid (5.00 g, 32.05 mmol), 1-adamantanecarboxylic acid (8.65 g, 48.03 mmol), 4-dimethylaminopyridine (1.95 g, 16.01 mmol) in dry $CH_2Cl_2$ (30 ml) was cooled to 0° C. and 1,3-dicyclohexylcarbodiimide (7.26 g, 35.22 mmol) added. The reaction mixture was stirred at room temperature overnight and filtered. The solid was washed with $CH_2Cl_2$ (150 ml) and the combined solution was washed with 2 N HCl solution (40 ml). The organic phase was dried over $MgSO_4$ and evaporated. The residue was crystallized from MeOH giving 5-(1-adamantanecarbonyl)-1,3-dimethyl-2,4,6(1H,3H,5H)-pyrimidinetrione 12 (7.10 g, 69%).

$R_f$ 0.57 (hexane/EtOAc/AcOH 15:5:0.1);

FAB MS $C_{17}H_{22}N_2O_4$ (318.37) m/z (%) 319 [M+H]$^+$ (100), 301 (33), 223 (13), 183 (94). $^1$H NMR (CDCl$_3$) d 19.23 (s, 1H, OH), 3.38, 3.35 (2s, 6H, 2 NCH$_3$), 2.18, 2.07 (2s, 12H, 6 CH$_2$), 1.79 (m, 3H, 3 CH).

EXAMPLE 10

5-Trichloroacetimino-1,3-dimethyl-2,4,6(1H,3H,5H)-pyrimidinetrione (Dtpe-NH$_2$) 13

A mixture of 1,3-dimethylbarbituric acid (5.00 g, 32.02 mmol), 4-dimethylaminopyridine (1.95 g, 16.01 mmol), 1,8-diazabicyclo[5.4.0]undec-7-ene/DBU/(10 drops) in dry CH$_2$Cl$_2$ (50 ml) was cooled to 0° C. and trichloroacetonitrile (13.87 g, 96.06 mmol) added dropwise in 15 min. The reaction mixture was stirred at 0° C. for 30 min then at room temperature for 3 h, diluted with CH$_2$Cl$_2$ (50 ml) and washed with 1 N KHSO$_4$ solution (10 ml). The organic phase was dried over MgSO$_4$ and evaporated. The residue was crystallized from MeOH giving 5-acetimino-1,3-dimethyl-2,4,6(1H,3H,5H)-pyrimidinetrione 13 (6.22 g, 65%).

R$_f$ 0.61 (EtOAc/hexane 1:1);

FAB MS C$_8$H$_8$Cl$_3$N$_3$O$_3$ (300.53) m/z (%) 322 [M+Na]$^+$ (10), 300 [M+H]$^+$ (100), 264 (43), 243 (17), 207 (11), 183 (17).

$^1$H NMR (CDCl$_3$) d 13.13, 7.83 (2s, 2H, 2 NH), 3.37, 3.33 (2s, 6H, 2 NCH$_3$).

EXAMPLE 11

5-(4-Carboxybutyryl)-1,3-Dimethyl-2,4,6(1H,3H,5H)-Pyrimidinetrione (Dtpp-OH) 10 and 1,5-bis-(1,3-Dimethyl-2,4,6-(1H,3H,5H)-Trioxopyrimidin-5-ylidene)-1,5-Dihydroxy Pentane 33

A mixture of 1,3-dimethylbarbituric acid (5.00 g, 32.02 mmol), 4-dimethylaminopyridine (9.789 g, 80.05 mmol) in dry CH$_2$Cl$_2$ (75 ml) was cooled to 0° C. and glutaric anhydride (4.38 g, 38.42 mmol) added. The reaction mixture was stirred overnight at room temperature, diluted with CH$_2$Cl$_2$ (150 ml) and washed with 2 N HCl solution (40 ml). The organic phase was dried over MgSO$_4$ and evaporated. The residue was crystallized from AcOH giving 1,5-bis-(1,3-dimethyl-2,4,6(1H,3H,5H)-trioxopyrimidin-5-ylidene)-1,5-dihydroxy pentane 33 (1.2 g).

R$_f$ 0.71 (CH$_2$Cl$_2$/MeOH/AcOH 96:3:1);

FAB MS C$_{17}$H$_{20}$N$_4$O$_8$ (408.36) m/z (%) 431 [M+Na]$^+$ (8), 409 [M+H]$^+$ (100).

$^1$H NMR (CDCl$_3$) d 17.67 (s, 2H, 2 OH), 3.37, 3.31 (2s, 12H, 4 NCH$_3$), 3.27 (t, 4H, 2 CH$_2$), 2.12 (m, 2H, CH$_2$).

The filtrate was evaporated and the residue was crystallized from toluene to give 5-(4-carboxybutyryl)-1,3-dimethyl-2,4,6(1H,3H,5H)-pyrimidinetrione 10 (2.10 g, 24%)

R$_f$ 0.66 (CH$_2$Cl$_2$/MeOH/AcOH 96:3:1);

FAB MS C$_{11}$H$_{14}$N$_2$O$_6$ (270.24) m/z (%) 293 [M+Na]$^+$ (10), 271 [M+H]$^+$ (100), 253 (76), 225 (22), 211 (20).

$^1$H NMR (CDCl$_3$) d 17.67 (s, 1H, OH), 3.37, 3.32 (2s, 6H, 2 NCH$_3$), 3.23 (t, 2H, CH$_2$), 2.48 (t, 2H, CH$_2$), 2.05 (m, 2H, CH$_2$).

EXAMPLE 12

N-[1-(1,3-dimethyl-2,4,6(1H,3H,5H)-trioxopyrimidin-5-ylidene)ethyl]1-butylamine 2

5-Acetyl-1,3-dimethyl-2,4,6(1H,3H,5H)-pyrimidinetrione (100 mg, 0.50 mmol) was dissolved in n-butylamine (10 ml) and stirred at room temperature overnight. The solvent was evaporated, the residue was washed with ether to give N-[1-(1,3-dimethyl-2,4,6(1H,3H,5H)-trioxopyrimidin-5-ylidene)ethyl] 1-butylamine 2 (121 mg, 95%)

R$_f$ 0.33 (EtOAc/hexane 2:1);

FAB MS C$_{12}$H$_{19}$N$_3$O$_3$ (253.28) m/z (%) 266 [M+Na]$^+$ (8), 254 [M+H]$^+$ (100), 195 (14).

$^1$H NMR (CDCl$_3$) d 12.55 (s, 1H, NH), 3.44 (m, 2H, CH$_2$), 3.31, 3.30 (2s, 6H, 2 NCH$_3$), 2.68 (s, 3H, CH$_3$), 1.69, 1.45 (2m, 4H, 2 CH$_2$), 0.97 (t, 3H, CH$_3$).

EXAMPLE 13

N-[1-(1,3-dimethyl-2,4,6(1H,3H,5H)-trioxopyrimidin-5-ylidene)phenylmethyl]1-butylamine 4

A mixture of 5-benzoyl-1,3-dimethyl-2,4,6(1H,3H,5H)-pyrimidinetrione (500 mg, 1.92 mmol) and N,N-diisopropylethylamine (248 mg, 1.92 mmol) in n-butylamine (10 ml) was refluxed for 2 hours. The solvent was evaporated, the residue was washed 1 M KHSO$_4$ solution, dried and evaporated. The residue was washed with ether to give N-[1-(1,3-dimethyl-2,4,6(1H,3H,5H)-trioxopyrimidin-5-ylidene)phenylmethyl] 1-butylamine 4 (575 mg, 95%)

R$_f$ 0.41 (EtOAc/hexane/TFA 10:15:0.1);

FAB MS C$_{17}$H$_{21}$N$_3$O$_3$ (315.36) m/z (%) 338 [M+Na]$^+$ (16), 316 [M+H]$^+$ (100), 307 (14).

$^1$H NMR (CDCl$_3$) d 12.42 (s, 1H, NH), 7.48 (m, 3H, 3 Ar—H), 7.17 (m, 2H, 2 Ar—H), 3.37, 3.15 (2s, 6H, 2 NCH$_3$), 3.04 (m, 2H, CH$_2$), 1.52, 1.32 (2m, 4H, 2 CH$_2$), 0.86 (t, 3H, CH$_3$).

EXAMPLE 14

N-[1-(1,3-dimethyl-2,4,6(1H,3H,5H)-trioxopyrimidin-5-ylidene)ethyl]glycine 14

A mixture of 5-acetyl-1,3-dimethyl-2,4,6(1H,3H,5H)-pyrimidinetrione (396 mg, 2.00 mmol), glycine (100 mg, 1.33 mmol) and N,N-diisopropyl-ethylamine (172 mg, 1.33 mmol) in abs. EtOH (10 ml) was stirred under reflux overnight. The solvent was evaporated, the residue was taken up in CH$_2$Cl$_2$ (100 ml), washed with 1 M KHSO$_4$ solution (10 ml). The resulting suspension was filtered, the precipitate was washed with ether and recrystallized from EtOH giving N-[1-(1,3-dimethyl-2,4,6(1H,3H,5H)-trioxopyrimidin-5-ylidene)-ethyl]glycine 14 (290 mg, 85%).

R$_f$ 0.28 (CH$_2$Cl$_2$/EtOAc/MeOH 10:7:1);

FAB MS C$_{10}$H$_{13}$N$_3$O$_5$ (255.22) m/z (%) 278 [M+Na]$^+$ (15), 256 [M+H]$^+$ (100), 210 (44).

$^1$H NMR (CDCl$_3$) d 12.58 (s, 1H, NH), 3.64 (s, 2H, CH$_2$), 3.34, 3.3(2s, 6H, 2 NCH$_3$), 2.69 (s, 3H, CH$_3$).

EXAMPLE 15

N-[1-(1,3-dimethyl-2,4,6(1H,3H,5H)-trioxopyrimidin-5-ylidene)phenylmethyl]glycine 15

A mixture of 5-benzoyl-1,3-dimethyl-2,4,6(1H,3H,5H)-pyrimidinetrione (519 mg, 2.00 mmol), glycine (100 mg, 1.33 mmol) and N,N-diisopropylethyl-amine (172 mg, 1.33 mmol) in abs. EtOH (10 ml) was stirred under reflux overnight. The solvent was evaporated, the residue was taken up in CH$_2$Cl$_2$ (100 ml), washed with 1 M KHSO$_4$ solution (10 ml), dried over MgSO$_4$ and evaporated. The residue was suspended with ether to give N-[1-(1,3-dimethyl-2,4,6(1H,3H,5H)-trioxopyrimidin-5-ylidene)-phenylmethyl]glycine 15 (360 mg, 86%).

$R_f$ 0.38 ($CH_2Cl_2$/EtOAc/MeOH 10:7:1);

FAB MS $C_{15}H_{15}N_3O_5$ (317.29) m/z (%) 318 [M+H]$^+$ (60), 272 (15), 130 (100).

$^1$H NMR (DMSO-d$_6$) d 12.30 (t, 1H, NH), 7.43 (m, 3H, 3 Ar—H), 7.14 (m, 2H, 2 Ar—H), 3.76 (d, 2H, $CH_2$), 3.20, 2.93 (2s, 6H, 2 NCH$_3$).

EXAMPLE 16

N-[1-(1,3-dimethyl-2,4,6(1H,3H,5H)-trioxopyrimidin-5-ylidene)phenylethyl]glycine 16

A mixture of 5-phenylacetyl-1,3-dimethyl-2,4,6(1H,3H,5H)-pyrimidinetrione (548 mg, 2.00 mmol), glycine (100 mg, 1.33 mmol) and N,N-diisopropylethyl-amine (172 mg, 1.33 mmol) in abs. EtOH (10 ml) was stirred under reflux overnight. The solvent was evaporated, the residue was taken up in $CH_2Cl_2$ (100 ml), washed with 1 M KHSO$_4$ solution (10 ml), dried over MgSO$_4$ and evaporated. The residue was suspended with ether to give N-[1-(1,3-dimethyl-2,4,6(1H,3H,5H)-trioxopyrimidin-5-ylidene)phenylethyl]glycine 16 (360 mg, 81%).

$R_f$ 0.40 ($CH_2Cl_2$/EtOAc/MeOH 10:7:1);

FAB MS $C_{16}H_{17}N_3O_5$ (331.32) m/z (%) 354 [M+Na]$^+$ (15), 332 [M+H]$^+$ (80), 286 (20), 130 (100).

$^1$H NMR (CDCl$_3$) d 13.05 (s, 1H, NH), 7.32–7.16 (m, 5H, 5 Ar—H), 4.69 (s, 2H, CH$_2$Ar), 4.14 (d, 2H, $CH_2$), 3.37, 3.29 (2s, 6H, 2 NCH$_3$).

EXAMPLE 17

Cleavage of 5-acyl-1,3-dimethylbarbituric acid protected primary amines affording 5-acyl-1,3-dimethylbarbituric acid protected hydroxylamines 34

N-[1-(1,3-Dimethyl-2,4,6(1H,3H,5H)-trioxopyrimidin-5-ylidene)phenylmethyl]hydroxylamine 17 and Benzyl 2-deoxy-2-amino-α-D-glucopyranoside 34 Benzyl 2-deoxy-2-[1-(1,3-dimethyl-2,4,6(1H,3H,5H)-trioxo-pyrimidin-5-ylidene)phenylmethylamino]-α-D-glucopyranoside 22 (100 mg, 0.19 mmol) in NH$_2$OH/MeOH (20%, 10 ml) was stirred at room temperature for 30 min. The solution was evaporated, the residue was suspended with ether (20 ml) and filtered to give benzyl 2-deoxy-2-amino-α-D-glucopyranoside 34 (45 mg, 90%).

$R_f$ 0.11 ($CH_2Cl_2$/EtOAc/MeOH 10:7:3);

FAB MS $C_{13}H_{19}NO_5$ (269.28) m/z (%) 292 [M+Na]$^+$ (45), 270 [M+H]$^+$ (100), 253 (20), 178 (18).

$^1$H NMR (DMSO-d$_6$) d 7.35–7.25 (m, 5H, 5 Ar—H), 4.91, 4.56 (2s, 2H, 2 NH), 4.73 (d, 1H, H–1, $J_{1,2}$=3.44 Hz), 4.66, 4.40 (2d, 2H, CH$_2$Ar), 3.61–3.05 (5 sugar-H), 2.40 (dd, 1H, H–2).

The filtrate was evaporated and purified by chromatography using $CH_2Cl_2$/EtOAc/MeOH 10:7:1 to afford N-[1-(1,3-dimethyl-2,4,6(1H,3H,5H)-trioxopyrimidin-5-ylidene)phenylmethyl]hydroxylamine 17 (40 mg, 73%).

$R_f$ 0.76 ($CH_2Cl_2$/EtOAc/MeOH 10:7:3);

FAB MS $C_{13}H_{14}N_4O_3$ (275.25) m/z (%) 298 [M+Na]$^+$ (13), 276 [M+H]$^+$ (100), 243 (20).

$^1$H NMR (CDCl$_3$) d 13.95 (s, 1H, NH), 7.32–7.16 ((m, 5H, 5 Ar—H), 3.39, 3.14 (2s, 6H, 2 NCH$_3$).

EXAMPLE 18

N-[1-(1,3-dimethyl-2,4,6(1H,3H,5H)-trioxopyrimidin-5-ylidene)phenylmethyl]acetic hydrazide 18

A mixture of 5-benzoyl-1,3-dimethyl-2,4,6(1H,3H,5H)-pyrimidinetrione 3 (260 mg, 1.00 mmol) and acetic hydrazide (222 mg, 3.00 mmol) in abs. EtOH (10 ml) was stirred under reflux overnight. The solvent was evaporated, the residue was taken up in $CH_2Cl_2$ (100 ml), washed with 1 M KHSO$_4$ solution (10 ml), dried over MgSO$_4$ and evaporated. The residue was crystallized from MeOH to give N-[1-(1,3-dimethyl-2,4,6(1H,3H,5H)-trioxopyrimidin-5-ylidene)phenylmethyl]acetic hydrazide 18 (250 mg, 79%).

$R_f$ 0.42 (MeCN/CHCl$_3$ 2:1);

FAB MS $C_{15}H_{16}N_4O_4$ (316.31) m/z (%) 339 [M+Na]$^+$ (28), 317 [M+H]$^+$ (100)

$^1$H NMR (CDCl$_3$) d 13.84 (s, 1H, NH), 7.61 (s, 1H, NH), 7.49, 7.20 (2m, 5H, 5 Ar—H), 3.38, 3.13 (2s, 6H, 2 NCH$_3$), 1.77 (s, 3H, NAc)

EXAMPLE 19

Cleavage of 5-acyl-1,3-dimethylbarbituric acid protected primary amines affording 5-acyl-1,3-dimethylbarbituric acid protected hydrazines N-[1-(1,3-Dimethyl-2,4,6(1H,3H,5H)-Trioxopyrimidin-5-ylidene)phenylmethyl]hydrazine 19

Benzyl 2-deoxy-2-[1-(1,3-dimethyl-2,4,6(1H,3H,5H)-Trioxopyrimidin-5-ylidene)phenylmethyl-amino]-α-D-glucopyranoside 22 (100 mg, 0.19 mmol) in N$_2$H$_4$/MeOH (20%, 10 ml) was stirred at room temperature for 30 min. The solution was evaporated, the residue was suspended with ether (20 ml) and filtered to give benzyl 2-deoxy-2-amino-α-D-glucopyranoside 34 (45 mg, 90%).

$R_f$ 0.11 ($CH_2Cl_2$/EtOAc/MeOH 10:7:3);

The filtrate was evaporated, purified by chromatography using $CH_2Cl_2$/EtOAc/MeOH 10:7:3 as the mobile phase to give N-[1-(1,3-dimethyl-2,4,6(1H,3H,5H)-trioxopyrimidin-5-ylidene)phenylmethyl]hydrazine 19 (40 mg, 74%).

$R_f$ 0.66 ($CH_2Cl_2$/EtOAc/MeOH 10:7:3);

FAB MS $C_{13}H_{14}N_4O_3$ (274.25) m/z (%) 297 [M+Na]$^+$ (15), 275 [M+H]$^+$ (100), 243 (20).

$^1$H NMR (CDCl$_3$) d 13.75 (s, 1H, NH), 7.32–7.16 (m, 5H, 5 Ar—H), 3.38, 3.13 (2s, 6H, 2 NCH$_3$).

EXAMPLE 20

Cleavage of 5-acyl-1,3-dimethylbarbituric acid protected primary amines with ammonia affording amino-substituted 5-acyl-1,3-dimethylbarbituric acid 5-Benzoimino-1,3-dimethyl-2,4,6(1H,3H,5H)-pyrimidinetrione 20

Benzyl 2-deoxy-2-[1-(1,3-dimethyl-2,4,6(1H,3H,5H)-trioxopyrimidin-5-ylidene)phenylmethyl-amino]-α-D-glucopyranoside 22 (100 mg, 0.19 mmol) in 10 ml NH$_3$/MeOH was stirred at room temperature for 30 min. The solution was evaporated, the residue was suspended with ether (20 ml) and filtered to give benzyl 2-deoxy-2-amino-α-D-glucopyranoside 34 (48 mg, 92%).

$R_f$ 0.11 ($CH_2Cl_2$/EtOAc/MeOH 10:7:3);

The filtrate was evaporated to afford 5-benzo-imino-1,3-dimethyl-2,4,6(1H,3H,5H)-pyrimidinetrione 20 (47 mg, 93%).

$R_f$ 0.86 ($CH_2Cl_2$/EtOAc/MeOH 10:7:3);

FAB MS $C_{13}H_{13}N_3O_3$ (259.25) m/z (%) 282 [M+Na]$^+$ (35), 260 [M+H]$^+$ (100), 243 (20).

¹H NMR (CDCl₃) d 12.48 (s, 1H, NH), 7.32–7.16 (m, 5H, 5 Ar—H), 3.38, 3.30 (2s, 6H, 2 NCH₃).

EXAMPLE 21

Cleavage of 5-acyl-1,3-dimethylbarbituric acid protected primary amines with primary amines N-[1-(1,3-Dimethyl-2,4,6(1H,3H,5H)-trioxopyrimidin-5-ylidene)phenylmethyl]1-butylamine 4

Benzyl 2-deoxy-2-[1-(1,3-dimethyl-2,4,6-(1H,3H,5H)-trioxopyrimidin-5-ylidene)phenylmethylamino]-α-D-glucopyranoside 22 (100 mg, 0.19 mmol) in 10 ml n-BuNH₂ was stirred at room temperature for 30 min. The solution was evaporated, the residue was suspended with ether (20 ml) and filtered to give benzyl 2-deoxy-2-amino-α-D-glucopyranoside 34 (48 mg, 92%).

$R_f$ 0.11 (CH₂Cl₂/EtOAc/MeOH 10:7:3);

The filtrate was evaporated to afford N-[1-(1,3-dimethyl-2,4,6(1H,3H,5H)-trioxopyrimidin-5-ylidene)-phenylmethyl]1-butylamine 4 (50 mg, 94%).

$R_f$ 0.89 (CH₂Cl₂/EtOAc/MeOH 10:7:3);

EXAMPLE 22

Benzyl 2-deoxy-2-[1-(1,3-dimethyl-2,4,6(1H,3H,5H)-trioxopyrimidin-5-ylidene)ethylamino]-α-D-glucopyranoside 21

A mixture of 5-acetyl-1,3-dimethyl-2,4,6-(1H,3H,5H)-pyrimidinetrione 1 (220 mg, 1.11 mmol), benzyl 2-amino-2-deoxy-α-D-glucopyranoside 34 (200 mg, 0.74 mmol) and N,N-diisopropylethylamine (96 mg, 0.74mmol) in abs. EtOH (10 ml) was stirring under reflux overnight. The solvent was evaporated, the residue was taken up in CH₂Cl₂ (100 ml), washed with 1 M KHSO₄ solution (10 ml). The resulting suspension was filtered and the precipitate was washed with ether to give benzyl 2-deoxy-2-[1-(1,3-dimethyl-2,4,6-(1H,3H,5H)-trioxopyrimidin-5-ylidene)-ethylamino]-α-D-glucopyranoside 21 (245 mg, 73%).

$R_f$ 0.43 (CH₂Cl₂/EtOAc/MeOH 10:7:3);

FAB MS C₂₁H₂₇N₃O₈ (449.45) m/z (%) 472 [M+Na]⁺ (12), 450 [M+H]⁺ (100), 358 (25), 342 (66).

¹H NMR (DMSO-d₆) d 12.68 (d, 1H, NH), 7.46 (d, 2H, 2 Ar—H), 7.31 (m, 3H, 3 Ar—H), 4.95 (d, 1H, H–1, $J_{1,2}$=3.60 Hz), 3.19, 3.15 (2s, 6H, 2 NCH₃), 2.65 (s, 3H, CH₃).

EXAMPLE 23

Benzyl 2-deoxy-2-[1-(1,3-dimethyl-2,4,6(1H,3H,5H)-trioxopyrimidin-5-ylidene)phenylmethylamino]-α-D-glucopyranoside 22

A mixture of 5-benzoyl-1,3-dimethyl-2,4,6-(1H,3H,5H)-pyrimidinetrione 3 (290 mg, 1.11 mmol), benzyl 2-amino-2-deoxy-α-D-glucopyranoside 34 (200 mg, 0.74 mmol) and N,N-diisopropylethylamine (96 mg, 0.74 mmol) in abs. EtOH (10 ml) was stirred under reflux overnight. The solvent was evaporated, the residue was taken up in CH₂Cl₂ (100 ml), washed with 1 M KHSO₄ solution (10 ml) and evaporated. The residue was crystallized from MeCN to give benzyl 2-deoxy-2-[1-(1,3-dimethyl-2,4,6(1H,3H,5H)-trioxopyrimidin-5-ylidene)-phenylmethylamino]-α-D-glucopyranoside 22 (270 mg, 71%).

$R_f$ 0.35 (CH₂Cl₂/EtOAc/MeOH 10:7:1);

FAB MS C₂₆H₂₉N₃O₈ (511.51) m/z (%) 534 [M+Na]⁺ (18), 512 [M+H]⁺ (100), 420 (18), 404 (36), 338 (75).

¹H NMR (DMSO-d₆) d 12.47 (d, 1H, NH), 7.41–7.17 (m, 10H, 10 Ar—H), 4.66 (d, 1H, H–1, $J_{1,2}$=3.55 Hz), 4:68, 4.48 (2d, 2H, CH₂Ar), 2.99, 2.94 (2s, 6H, 2 NCH₃).

EXAMPLE 24

Benzyl 2-deoxy-2-[1-(1,3-dimethyl-2,4,6(1H,3H, 5H)-trioxopyrimidin-5-ylidene)(9-fluorenylmethylamino)]-α-D-glucopyranoside 23

A mixture of 5-(9-fluorenylcarbonyl)-1,3-dimethyl-2,4,6 (1H,3H,5H)-pyrimidinetrione 5 (388 mg, 1.11 mmol) and benzyl 2-amino-2-deoxy-α-D-glucopyrano-side 34 (200 mg, 0.74 mmol) in abs. EtOH (10 ml) was stirred under reflux overnight. The solvent was evaporated, the residue was taken up in CH₂Cl₂ (100 ml), washed with 1 M KHSO₄ solution (10 ml) and evaporated. The residue was purified by chromatography using CHCl₃/MeCN/AcOH 10:10:0.1 to give benzyl 2-deoxy-2-[1-(1,3-dimethyl-2,4,6(1H,3H,5H)-trioxopyrimidin-5-ylidene)(9-fluorenylmethylamino)]-α-D-glucopyranoside 23 (140 mg, 31%).

$R_f$ 0.37 (CHCl₃/MeCN/AcOH 10:10:0.1);

FAB MS C₃₃H₃₃N₃O₈ (599.61) m/z (%) 622 [M+Na⁺] (48), 600 [M+H]⁺ (100), 492 (88), 474 (26), 346 (75).

¹H NMR (CDCl₃) d 12.72 (d, 1H, NH), 7.85–6.77 (m, 14H, 13 Ar—H, CH), 4.57, 4.22 (2d, 2H, CH₂Ar), 3.47, 3.40 (2s, 6H, 2 NCH₃).

EXAMPLE 25

Benzyl 2-deoxy-2-(1-(1,3-dimethyl-2,4,6(1H,3H, 5H)-trioxopyrimidin-5-ylidene)phenylethylamino)-α-D-glucopyranoside 24

A mixture of 5-phenylacetyl-1,3-dimethyl-2,4,6(1H,3H, 5H)-pyrimidinetrione 8 (305 mg, 1.11 mmol), benzyl 2-amino-2-deoxy-α-D-glucopyranoside 34 (200 mg, 0.74 mmol) and N,N-diisopropylethylamine (96 mg, 0.74 mmol) in abs. EtOH (10 ml) was stirred under reflux overnight. The solvent was evaporated, the residue was taken up in CH₂Cl₂ (100 ml), washed with 1 M KHSO₄ solution (10 ml) and evaporated. The residue was purified by chromatography using CHCl₃/EtOAc/MeOH 10:7:1 as the mobile phase to give benzyl 2-deoxy-2-[1-(1,3-dimethyl-2,4,6(1H,3H,5H)-trioxopyrimidin-5-ylidene)-phenylethylamino]-α-D-glucopyranoside 24 (280 mg, 72%).

$R_f$ 0.47 (CHCl₃/EtOAc/MeOH 10:7:1);

FAB MS C₂₇H₃₁N₃O₈ (525.54) m/z (%) 548 [M+Na]⁺ (22), 526 [M+H]⁺ (100), 417 (52), 274 (47).

¹H NMR (DMSO-d₆) d 12.88 (d, 1H, NH), 7.41–7.01 (m, 10H, 10 Ar—H), 4.65, 4.39 (2d, 2H, CH₂Ar), 4.38 (d, 1H, H–1, $J_{1,2}$=3.03 Hz), 3.23, 3.09 (2s, 6H, 2 NCH₃).

EXAMPLE 26

Benzyl 2-deoxy-2-[1-(1,3-dimethyl-2,4,6(1H,3H, 5H)-trioxopyrimidin-5-ylidene)diphenylethylamino]-α-D-glucopyranoside 25

A mixture of 5-diphenylacetyl-1,3-dimethyl-2,4,6(1H, 3H,5H)-pyrimidinetrione 9 (390 mg, 1.11 mmol), benzyl 2-amino-2-deoxy-α-D-glucopyranoside 34 (200 mg, 0.74 mmol) and N,N-diisopropylethylamine (96 mg, 0.74 mmol) in abs. EtOH (10 ml) was stirred under reflux overnight. The solvent was evaporated, the residue was taken up in CH₂Cl₂

(100 ml), washed with 1 M KHSO$_4$ solution (10 ml) and evaporated. The residue was purified by chromatography using 1,2-dichloroethane-/MeOH/AcOH 10:1:0.1 as the mobile phase to give benzyl 2-deoxy-2-[1-(1,3-dimethyl-2,4,6(1H,3H,5H)-trioxo-pyrimidin-5-ylidene) diphenylethylamino]-α-D-glucopyranoside 25 (300 mg, R$_f$ 0.37 (1,2-dichloroethane/MeOH/AcOH 10:1:0.1);

FAB MS C$_{33}$H$_{35}$N$_3$O$_8$ (601.63) m/z (%) 624 [M+Na]$^+$ (20), 602 [M+H]$^+$ (100), 494 (47), 348 (42), 338 (39)

$^1$H NMR (CDCl$_3$) d 13.44 (d, 1H, NH), 8.15 (s, 1H, CHAr$_2$), 7.52–6.94 (m, 15H, 15 Ar—H), 4.55, 4.21 (2d, 2H, CH$_2$Ar), 3.39, 3.29 (2s, 6H, 2 NCH$_3$).

EXAMPLE 27

Benzyl 2-deoxy-2-[1(1,3-dimethyl-2,4,6(1H,3H, 5H)-trioxopyrimidin-5-ylidene)-(2,2-dimethylpentylamino)]-α-D-glucopyranoside 28

A mixture of 5-pivaloyl-1,3-dimethyl-2,4,6(1H,3H,5H)-pyrimidinetrione 11 (267 mg, 1.11 mmol), benzyl 2-amino-2-deoxy-α-D-glucopyranoside 34 (200 mg, 0.74 mmol) and N,N-diisopropylethylamine (96 mg, 0.74 mmol) in abs. EtOH (10 ml) was stirring under reflux overnight. The solvent was evaporated, the residue was taken up in CH$_2$Cl$_2$ (100 ml), washed with 1 M KHSO$_4$ solution (10 ml) and evaporated. The residue was purified by chromatography using CH$_2$Cl$_2$/EtOAc/MeOH 10:7:3 as the mobile phase to give benzyl 2-deoxy-2-[1-(1,3-dimethyl-2,4,6(1H,3H,5H)-trioxopyrimidin-5-ylidene)-(2,2-dimethylpentylamino)]-α-D-glucopyranoside 28 (240 mg, 66%).

R$_f$ 0.47 (CH$_2$Cl$_2$/EtOAc/MeOH 10:7:3);

FAB MS C$_{24}$H$_{33}$N$_3$O$_8$ (491.52) m/z (%) 514 [M+Na]$^+$ (28), 492 [M+H]$^+$ (100), 270 (25), 240 (54).

$^1$H NMR (CDCl$_3$) d 12.76 (d, 1H, NH), 7.29 (m, 5H, 5 Ar—H), 4.64, 4.40 (2d, 2H, CH$_2$Ar), 3.24, 3.21 (2s, 6H, 2 NCH$_3$), 1.37 (s, 9H, 3 CH$_3$).

EXAMPLE 28

Benzyl 2-deoxy-2-[1-(1,3-dimethyl-2,4,6 (1H,3H, 5H)-Trioxopyrimidin-5-ylidene)-(1-adamantylmethylamino)]-α-D-glucopyranoside 29

A mixture of 5-adamantanecarbonyl-1,3-dimethyl-2,4,6 (1H,3H,5H)-pyrimidinetrione 12 (709 mg, 2.23 mmol), benzyl 2-amino-2-deoxy-α-D-glucopyranoside 34 (200 mg, 0.74 mmol) and N,N-diisopropylethylamine (288 mg, 2.23 mmol) in abs. EtOH (10 ml) was stirred under reflux overnight. The solvent was evaporated, the residue was taken up in CH$_2$Cl$_2$ (100 ml), washed with 1 M KHSO$_4$ solution (10 ml) and evaporated. The residue was suspended with ether to give benzyl 2-deoxy-2-[1-(1,3-dimethyl-2,4,6 (1H,3H,5H)-trioxopyrimidin-5-ylidene)-(1-adamantylmethylamino)]-α-D-glucopyranoside 29 (260 mg, 62%).

R$_f$ 0.45 (CH$_2$Cl$_2$/EtOAc/MeOH 10:7:3);

FAB MS C$_{30}$H$_{39}$N$_3$O$_8$ (569.63) m/z (%) 592 [M+Na]$^+$ (60), 570 [M+H]$^+$ (100).

$^1$H NMR (CDCl$_3$) d 12.74 (d, 1H, NH), 7.33 (m, 5H, 5 Ar—H), 4.65, 4.43 (2d, 2H, CH$_2$Ar), 3.27, 3.22 (2s, 6H, 2 NCH$_3$), 2.13, 2.04 (2s, 12H, 6 CH$_2$), 1.72 (m, 3H, 3 CH).

EXAMPLE 29

Reaction of primary amines with 5-trichloroacetimino-1,3-dimethyl-2,4,6(1H,3H,5H)-pyrimidinetrione Benzyl 2-deoxy-2-[1-(1,3-dimethyl-2,4,6(1H,3H, 5H)-trioxopyrimidin-5-ylidene)aminomethylamino]-α-D-glucopyranoside 27

A mixture of 5-Trichloroacetimino-1,3-dimethyl-2,4,6 (1H,3H,5H)-pyrimidinetrione 13 (333 mg, 1.11 mmol), benzyl 2-amino-2-deoxy-α-D-glucopyranoside 34 (200 mg, 0.74 mmol) and N,N-diisopropylethylamine (96 mg, 0.74 mmol) in abs. EtOH (10 ml) was stirred under reflux overnight. The solvent was evaporated, the residue was taken up in CH$_2$Cl$_2$ (100 ml), washed with 1 M KHSO$_4$ solution (10 ml) and evaporated. The residue was purified by chromatography using CH$_2$Cl$_2$/EtOAc/MeOH 10:7:3 as the mobile phase to give benzyl 2-deoxy-2-[1-(1,3-dimethyl-2,4,6(1H,3H,5H)-trioxopyrimidin-5-ylidene) aminomethylamino]-α-D-glucopyranoside 27 (250 mg, 75%).

R$_f$ 0.41 (CH$_2$Cl$_2$/EtOAc/MeOH 10:7:3);

FAB MS C$_{20}$H$_{26}$N$_4$O$_8$ (450.44) m/z (%) 473 [M+Na]$^+$ (21), 451 [M+H]$^+$ (100), 358 (15), 342 (74), 265 (269).

$^1$H NMR (DMSO-d$_6$) d 10.86 (d, 1H, NH), 10.06 (s, 1H, NH), 7.74 (s, 1H, NH), 7.42 (d, 2H, 2 Ar—H), 7.29 (m, 3H, 3 Ar—H), 4.87 (d, 1H, H–1, J$_{1,2}$=3.22 Hz), 4.69, 4.48 (2d, 2H, CH$_2$Ar).

EXAMPLE 30

Preparation of "Linker-Carbohydrate Conjugate"

Benzyl 2-deoxy-2-[1-(1,3-dimethyl-2,4,6(1H,3H, 5H)-trioxopyrimidin-5-ylidene)(4-carboxybutylamino)]-α-D-glucopyranoside 26

A mixture of 5-(4-carboxybutyryl)-1,3-dimethyl-2,4,6 (1H,3H,5H)-pyrimidinetrione 10 (301 mg, 1.11 mmol), benzyl 2-amino-2-deoxy-α-D-glucopyranoside (200 mg, 0.74 mmol) and N,N-diisopropylethylamine (240 mg, 1.85 mmol) in abs. EtOH (10 ml) was stirred under reflux overnight. The solvent was evaporated, the residue was taken up in CH$_2$Cl$_2$ (100 ml) and washed with 1 M KHSO$_4$ solution (10 ml). The resulting suspension was filtered, the precipitate was washed with ether giving benzyl 2-deoxy-2-[1-(1,3-dimethyl-2,4,6(1H,3H,5H)-trioxopyrimidin-5-ylidene)(4-carboxybutylamino)]-α-D-glucopyranoside 26 (280 mg, 73%).

R$_f$ 0.28 (CH$_2$Cl$_2$/EtOAc/MeOH 10:7:5);

FAB MS C$_{24}$H$_{31}$N$_3$O$_{10}$ (521.51) m/z (%) 544 [M+Na]$^+$ (25), 522 [M+H]$^+$ (100), 430 (21), 414 (75).

$^1$H NMR (DMSO-d$_6$) d 12.70 (d, 1H, NH), 7.45–7.18 (m, 5H, 5 Ar—H), 4.97 (d, 1H, H–1, J$_{1,2}$=3.47 Hz), 4.97, 4.4.72 (2d, 2H, CH$_2$Ar), 3.17, 3.14 (2s, 6H, 2 NCH$_3$), 3.00 (t, 2H, CH$_2$), 2.34 (m, 4H, 2 CH$_2$).

EXAMPLE 31

Chiral 5-acyl-1,3-dimethylbarbituric acid derivatives for primary amine protection N,N'-Bis-(benzyl 2-deoxy-α-D-glucopyranosid-2-yl)-[5-(2-aminoacetimino)-1,3-dimethyl-2,4,6(1H, 3H 5H)-pyrimidinetrione] 30 and 5-[N-(benzyl 2-deoxy-α-D-glucopyranosid-2-yl)aminoacetyl]-1,3-dimethyl-2,4,6(1H,3H,5H)-pyrimidinetrione 31

A mixture of 5-chloroacetyl-1,3-dimethyl-2,4,6(1H,3H, 5H)-pyrimidinetrione 6 (260 mg, 1.11 mmol), benzyl 2-amino-2-deoxy-α-D-glucopyranoside 34 (200 mg, 0.74 mmol) and N,N-diisopropylethylamine (96 mg, 0.74 mmol) in abs. EtOH (10 ml) was stirred under reflux overnight. The solvent was evaporated, the residue was taken up in CH$_2$Cl$_2$ (100 ml), washed with 1 M KHSO$_4$ solution (10 ml) and evaporated. The residue was purified by chromatography using CH$_2$CH$_2$/EtOAc/MeOH 10:7:3 as the mobile phase to give N,N'-bis-(benzyl 2-deoxy-α-D-glucopyranosid-2-yl)-

[5-(2-aminoacetimino)-1,3-dimethyl-2,4,6(1H,3H,5H)-pyrimidinetrione] 30 (110 mg, 21%).

$R_f$ 0.42 ($CH_2Cl_2$/EtOAc/MeOH 10:7:3);

FAB MS $C_{34}H_{44}N_4O_{13}$ (716.72) m/z (%) 739 [M+Na]$^+$ (22), 717 [M+H]$^+$ (100).

$^1$H NMR (DMSO-d$_6$) d 12.58 (d, 1H, NH), 7.43–7.25 (m, 10H, 10 Ar—H), 4.65–4.24 (4d, 4H, 2 $CH_2$Ar), 3.18, 3.08 (2s, 6H, 2 $NCH_3$), and 5-[N-(benzyl 2-deoxy-α-D-glucopyranosid-2-yl)aminoacetyl]-1,3-dimethyl-2,4,6(1H,3H,5H)-pyrimidinetrione 30 (80 mg, 23%).

$R_f$ 0.33 ($CH_2Cl_2$/EtOAc/MeOH 10:7:3);

FAB MS $C_{21}H_{27}N_3O_9$ (465.45) m/z (%) 488 [M+Na]$^+$ (27), 466 [M+H]$^+$ (100).

$^1$H NMR (DMSO) d 17.22 (s, 1H, OH), 7.41–7.27 (m, 5H, 5 Ar—H), 4.68, 4.46 (2d, 2H, $CH_2$Ar), 3.19, 3.14 (2s, 6H, 2 $NCH_3$).

EXAMPLE 32

Preparation of Resin-linker-carbohydrate conjugate

Benzyl 2-deoxy-2-[1-(1,3-dimethyl-2,4,6(1H,3H,5H)-trioxopyrimidin-5-ylidene)(4-carboxybutylamino)]-3,4,6-tri-O-acetyl-α-D-glucopyranoside—MBHA resin conjugate 32

Benzyl 2-deoxy-2-[1-(1,3-dimethyl-2,4,6(1H,3H,5H)-trioxopyrimidin-5-ylidene)(4-carboxybutylamino)]-α-D-glucopyranoside 26 (300 mg, 1.11 mmol) was dissolved in pyridine (10 ml), cooled to 0° C. and acetic anhydride (7 ml) added. The reaction mixture was stirred at room temperature overnight. The solvent was evaporated and the resulting residue was taken up in $CH_2Cl_2$ (70 ml), washed with 1 M $KHSO_4$ solution, dried over $MgSO_4$ and evaporated. The residue was taken up in DMF (10 ml) and was used as a reagent during the resin work. MBHA resin (Subst. ratio: 0.42 mmol/g) (200 mg) bearing a total amine functionality of 0.084 mmol was swelled in DMF for 20 min. The resin was then washed with fresh DMF and benzyl 2-deoxy-2-[1-(1,3-dimethyl-2,4,6(1H,3H,5H)-trioxopyrimidin-5-ylidene)(4-carboxybutylamino)]-3,4,6-tri-O-acetyl-α-D-glucopyranoside DMF solution (5 ml, 6.6 equiv.) and N,N'-diisopropylcarbodiimide (88 ml, 6.6 equiv.) were added and the resin gently agitated for 30 min. The TNBS test was faintly positive so using the above conditions, a double coupling was performed, this time producing a negative TNBS test result. The resin was washed with DMF, methanol and finally ether. The resin was then allowed to dry in vacuum over KOH overnight.

EXAMPLE 33

Carbohydrate Deprotection and Cleavage of the "Fully Protected Sugar—Linker—Resin Conjugate" Providing an "Amino Substituted Resin-Linker Conjugate" 35

The resin from Example 32 was gently agitated with sodium methoxide (100 mg, 1.85 mmol) in abs. MeOH (5 ml) at room temperature for 1 h. The resin was washed with abs. MeOH (5×10 ml), DMF (5×10 ml), ether (5×10 ml) and dried under high vacuum for 1 h, giving the resin bonded unprotected benzyl 2-amino-2-deoxy-α-D-glucopyranoside. A sample of resin (5 mg) was cleavaged by saturated $NH_3$/MeOH (0.2 ml) at room temperature for 10 min. The resin was filtered off, the filtrate was evaporated giving benzyl 2-amino-2-deoxy-α-D-glucopyranoside 34 in quantitative yield. During the cleavage conditions the resin was transformed into its amino-substituted form 35.

EXAMPLE 34

Preparation of "Resin-linker-carbohydrate Conjugate" Using "Amino-substituted resin-linker Conjugate"

"Amino-substituted resin-linker conjugate" 35 (100 mg, 0.042 mmol amine functionality), benzyl 2-amino-2-deoxy-α-D-glucopyranoside 34 (34 mg, 0.13 mmol) and diisopropylethylamine (16 mg, 0.126 mmol) in abs. EtOH gently stirred under reflux overnight. The reaction mixture was filtered, the resin was washed with MeOH, DMF, $CH_2Cl_2$, ether and dried to give the "resin-linker-carbohydrate conjugate" 37.

EXAMPLE 35

Preparation of a "Hydroxy-substituted Resin-linker Conjugate" 36

MBHA resin (Subst. ratio: 0.42 mmol/g) (200 mg) bearing a total amine functionality of 0.084 mmol was swelled in DMF for 20 min. The resin was then washed with fresh DMF and 5-(4-carboxybutyryl)-1,3-dimethyl-2,4,6(1H,3H,5H)-pyrimidinetrione 10 (68 mg, 0.25 mmol) and N,N'-diisopropylcarbodiimide (40 ml, 3.0 equiv.) were added in DMF (5 ml) and the resin gently agitated for 30 min. The TNBS test was faintly positive so using the above conditions, a double coupling was performed, this time producing a negative TNBS test result. The resin was washed with DMF, methanol and finally ether. The resin was then allowed to dry in vacuum over KOH overnight to give 36.

EXAMPLE 36

Preparation of a "Hydroxy-substituted Resin-linker Conjugate" Using "Amino-substituted Resin-linker Conjugate" 36

"Amino-substituted resin-linker conjugate" 35 (50 mg, 0.021 mmol amine functionality) was stirred at room temperature in 1 M NaOH solution (2.0 ml) for 10 min. The mixture was filtered, washed with $H_2O$, methanol and finally ether. The resin was then allowed to dry in vacuum over KOH overnight to give 36.

EXAMPLE 37

Preparation of "2-acetyl-1,3-indanedione" 38

A mixture of 4-dimethylaminopyridine (664 mg, 5.44 mmol), triethylamine (7.6 ml 54.56 mmol), acetic anhydride (6.2 ml, 65.48 mmol in dry 1,2-dichloroethane (60,ml) was stirred at −20° C. and a solution of 1,3-indanedione (7.96 g, 54.56 mmol) in 1,2-dichloroethane was added dropwise in 1.5 h. The reaction mixture was stirred for 30 min, then washed with 10% hydrochloric acid (80 ml) and twice with water (80 ml). The organic phase was dried over $MgSO_4$ and evaporated. The residue was crystallized from methyl-tert-butylether (50 ml) to give 2-acetyl-1,3-indanedione 38(6.5 g 63%). $R_f$ 0.27 (hexane-ethylacetate-acetic acid 20-5-0.5) MS $C_{11}H_8O_3$ m/z (%) 189 [M+H]$^+$ (100), 166 (72), 104 (20).

EXAMPLE 38

Methyl2-deoxy-2-[1-(1,3-dimethyl-2,4,6(1H,3H,5H)-trioxopyrimidin-5-ylidene)ethylamino]-1-thio-b-D-glucopyranoside 39

Methyl 2-deoxy-2-amino-1-thio-β-D-glucopyranoside (5.00 g, 23.9 mmol) was dissolved in dry ethanol (70 ml) and 1,3-dimethylbarbituric acid (9.47 g, 47.8 mmol) added to form a suspension. Triethylamine (5.40 g, 53.3 mmol) was then added and the resultant clear solution heated at reflux for 14 h. The solvent was evaporated, the residue dissolved in dichloromethane (200 ml) and 5% hydrochloric acid solution (200 ml) added. The resultant precipitate was collected and recrystallized from ethyl acetate to yield Methyl 2-deoxy-2-[1-(1,3-dimethyl-2,4,6(1H,3H,5H)-trioxopyrimidin-5-ylidene)ethylamino]-1-thio-β-D-glucopyranoside 39, as a colourless solid (7.82 g, 84.1%)

$R_f$ 0.57 ($CH_3CN/H_2O$ 9:1);

ESI-MS MS m/z 390.0 (M+H);

$^1$H NMR ($CDCl_3$) d 4.650 (d, 3H, $J_{1,2}$=9.9 Hz, H1), 3.894 (dd, 1H, H–3), 3.716 (dd, 1H, H–4), 3.547 (dd, 1H, H–2), 3.426 (d, 2H, H–6), 3.306 (m, 1H, H–5), 3.266 (s, 6H, 2×N—$CH_3$), 2.730 (s, 3H, vinylic-$CH_3$), 2.211 (s, 3H, S—$CH_3$).

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Bergman, M. and Zervas, L. Ber. Dtsc. Chem. Ges., 1932 65 1192

Branchaud, B. P. J. Org. Chem., 1983 48 3538.

Bycroft, B. W., Chan, W. C., Chhabra, S. R., Teesdale-Spittle, S. R. and Hardy, P. H. J. Chem. Soc. Chem Commun., 1993 777.

Bycroft, B. W., Chan, W. C., Chhabra, S. R. and Hone, N. D. J. Chem. Soc. Chem. Commun., 1993 778.

Carpino, A. L., Tsao, J.-H., Ringsdorf, H., Fell, E. and Gettrich, J. G. J. Chem. Soc. Chem. Common., 1978, 358.

Chan, W. C., Bycroft, B. W., Evans, D. J. and White, P. D. J. Chem. Soc. Chem. Commun., 1995 2209.

Colvin, E. W., McGarry, D. and Nugent, M. J. Tetrahedron Lett., 1988 44 4157.

Fischer, E. and Livschitz, W. Ber. Dtsch. Chem. Ges., 1915 48 360.

Goerdeler, J. and Holst, A. Angew. Chem., 1959 71 775.

Goldstein, S. W., Overman, L. E. and Rabinowitz, M. H. J. Org. Chem., 1992 57 1179.

Gribble, G. W., Saulnier, M. G., Obaza-Nutaitis, J. A. and Ketcha, D. M. J. Org. Chem., 1992 57 1581.

Halpern, B. and James, L. B. Aust. J. Chem., 1964 17 1282.

Hoppe. D. and Beckmann, L. Liebigs Ann. Chem., 1979 2066.

Kellam, B. Ph.D. Dissertation, 1996.

Kessler, W. and Iselin, B. Helv. Chim. Acta., 1966 49 1330.

Koskinen, A. M. and Rapoport, H. J. Org. Chem., 1989 54 1859.

Kunz, H. and Unverzagt, C. Angew. Chem. Int. Ed. Eng., 1984 23 436

McKay, F. C. and Albertson, N. F. J. Am Chem. Soc., 1957 79 4686

Mosher, W. A. and Meier, W. E. J. Org. Chem., 1970 35 2924.

Nicolaou, K. C., Bockovich, N. J, Carcanague, D. R., Hummel, C. W. and Iven, L. F. J. Am. Chem. Soc., 1992 114 8701

Overman, L. E., Okazaki, M. E. and Mishra, P. Tetrahedron Lett., 1986 27 4391.

Polt, R., Szabo, L., Treiberg, J., Li, Y., Hruby, V. J. J. Am. Chem. Soc., 1992 114 10249.

Sieber, P. and Riniker, B. Tetrahedron Lett., 1991 32 739.

Weinreb, S. M., Demko, D. M., Lessen, T. A. and Demers. J. P. Tetrahedron Lett., 1986 27 2099

Weygand, F. and Czendes, E. Angew Chem., 1952 64 136

Windholz, T. B. and Johnston, D. B. R. Tetrahedron Lett., 1967 2555.

What is claimed is:

1. A compound of formula V

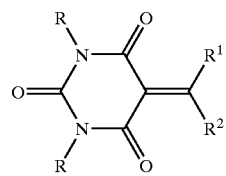

in which each R is independently H, substituted or unsubstituted alkyl, aryl, cycloalkyl, heteroalkyl, heteroaryl, or heterocycloalkyl;

$R^1$ is hydrogen; an alkyl, alkenyl, alkynyl, heteroalkyl, aryl, heteroaryl, cycloheteroaryl, cycloalkyl, heterocycloalkyl, alkanal, or thioalkanal group, each of which may be unsubstituted or substituted with a substituent selected from amino azido, halogen, hydroxyl, guanidino, carboxy, carboxylic acid ester, thio, carboxamide, alkylamino, dialkylamino, trialkylammonium, and alkoxy; with the provisos that (a) when $R^1$ is hydrogen, then $R^2$ is a protected, unprotected or substituted sugar amino-; a glycosylamino-, or a glycosylamino group of an oligosaccharide; a mono- or oligosaccharide coupled through a substituted or unsubstituted alkylamino-, arylamino-, cycloalkylamino, heteroalkylamino, heteroarylamino or heterocycloalkylamino group; an amino sugar; an amino acid or a peptide linked via a nitrogen atom; and (b) when $R^1$ is an alkyl, alkenyl, alkynyl, heteroalkyl, aryl, heteroaryl, cycloheteroaryl, cycloalkyl, heterocycloalkyl, alkanal, or thioalkanal group, each of which may be substituted or unsubstituted, then $R^2$ is a protected, unprotected or substituted sugar amino-; a glycosylamino-, or a glycosylamino group of an oligosaccharide; a mono- or oligosaccharide coupled through a substituted or unsubstituted alkylamino-, arylamino-, cycloalkylamino, heteroalkylamino, heteroarylamino or heterocycloalkylamino group; an amino sugar; an amino acid or a peptide linked via a nitrogen atom; an alkylamino, dialkylamino, arylamino, or diarylamino group, each of which may be substituted or unsubstituted.

2. A compound of claim 1, wherein $R^2$ is an oligosaccharide-O—$CH_2$—($C_6H_4$)—NH—, monosaccharide-O—$CH_2$—($C_6H_4$)—NH—, oligosaccharide-$CO_2CH_2$—($C_6H_4$)NH—, or monosaccharide-$CO_2CH_2$—($C_6H_4$)—NH— group.

3. A linker-saccharide complex, comprising a linker group and a compound according to claim 1.

4. A method of solution phase synthesis of oligosaccharides, comprising sequentially linking mono- or oligosaccharide groups to a compound according to claim 1.

5. A method according to claim 4, wherein combinatorial synthesis of aminoglycosides is performed.

6. A kit for solution phase synthesis or combinatorial synthesis of oligosaccharides, comprising a compound according to claim 1.

7. The kit of claim 6, further comprising one or more protecting agents, deprotecting agents, or solvents suitable for solid phase or combinatorial synthesis.

8. A compound according to claim 1, wherein each R group has 1 to 6 carbon atoms.

9. A compound according to claim 1, wherein each R group has 1 to 4 carbon atoms.

10. A compound according to claim 1, wherein the compound is chiral.

11. A method of preparing a compound according to claim 1, comprising the step of reacting an amine containing molecule with a compound of formula V wherein R and $R^1$ are as defined in claim 1 and $R^2$ is a leaving group selected from OH, Cl, dialkylamino and diarylamino.

12. A support of formula VII for solid-phase synthesis of oligosaccharides, peptides, or organic compounds, comprising a resin and a linker covalently attached to the resin:

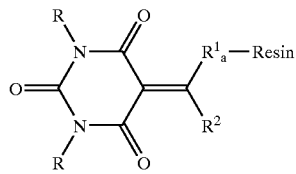

VII wherein
$R^1_a$ is a substituted or unsubstituted alkyl, cycloalkyl, heteroalkyl, heteroaryl, heterocycloalkyl or carboxylamido spacer group that is directly coupled to the resin support, or that may be coupled to the resin support via a suitable covalent linkage, which is stable to conditions of oligosaccharide synthesis and cleavage,
and $R^2$ is a protected, unprotected or substituted sugar amino-; a glycosylamino-, or a glycosylamino group of an oligosaccharide; a mono- or oligosaccharide coupled through a substituted or unsubstituted alkylamino-, arylamino-, cycloalkylamino, heteroalkylamino, heteroarylamino or heterocycloalkylamino group; an amino sugar; an amino acid or a peptide linked via a nitrogen atom; or an alkylamino, dialkylamino, arylamino, or diarylamino group, each of which may be substituted or unsubstituted.

13. A support according to claim 12, wherein the covalent linkage is provided by a —CONH—, —O—, —S—, —NH—, —COO—, —COS—, —CH=N, —NHCONH—, —NHCSNH or —NHNH— grouping.

14. A support according to claim 12 wherein the resin swells in water or in an organic solvent, and that comprises one of the following substituents: halogen, hydroxy, carboxyl, SH, $NH_2$, formyl, $SO_2NH_2$, or $NHNH_2$.

15. A method of solid-phase synthesis of oligosaccharides, comprising sequentially linking mono- or oligosaccharide groups to the support according to claim 12.

16. A method according to claim 15, wherein
(a) the linker is synthesised directly on the resin in a stepwise manner prior to the coupling of the initial sugar group, or
(b) the linker-initial sugar conjugate is synthesised in solution phase and subsequently coupled to the solid support, with subsequent sugars being sequentially attached.

17. A method according to claim 15, wherein the support comprises a resin, a linker and a saccharide selected from the group consisting of monosaccharides, oligosaccharides, aminosaccharides and aminooligosaccharides.

18. A method according to claim 15, wherein the second and all subsequent sugar groups are coupled to the oligosaccharide chain-resin conjugate after the last sugar in the oligosaccharide chain is partially deprotected.

19. A method according to claim 15, wherein the first sugar attached to the resin-linker unit is an unprotected, partially protected or fully protected glycoside, aminoglycoside, ether-linked sugar, or amino-linked sugar.

20. A method according to claim 19, wherein the first sugar coupled to the resin is an aminosugar, an aminoglycoside or an amino-oligosaccharide, or a glycosyl amine of an oligosaccharide.

21. A method according to claim 15, wherein the oligosaccharide is branched, and deprotection is achieved by using one or more protecting groups selected from the group consisting of acyl-type, trityl, methoxytrityl, methoxybenzyl, silyl and photolabile protecting groups in addition to permanent ether-type protecting groups.

22. A kit for solid phase synthesis or combinatorial synthesis, comprising
(a) the support according to claim 12; or
(b) the compound according to claim 1.

23. The kit of claim 22, further comprising one or more protecting agents, deprotecting agents, or solvents suitable for solid phase or combinatorial synthesis.

* * * * *

UNITED STATES PATENT AND TRADEMARK OFFICE
CERTIFICATE OF CORRECTION

PATENT NO. : 6,765,089 B1
DATED : July 20, 2004
INVENTOR(S) : Toth et al.

Page 1 of 1

It is certified that error appears in the above-identified patent and that said Letters Patent is hereby corrected as shown below:

Title page,
Item [54], Title, delete "PROTECTING AND LINKING GROUPS FOR ORGANIC SYNTHESIS ON SOLID SUPPORTS" and insert -- PROTECTING AND LINKING GROUPS FOR ORGANIC SYNTHESIS -- therefor.

Column 30,
Lines 11-19, delete the structure and insert the following structure in which the placement of "V" has been corrected so that this number is properly shown below the structure and not to the upper right.

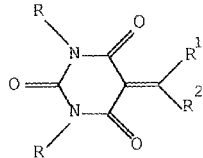

V

Column 31,
Lines 20-29, delete the structure and insert the following structure in which the placement of "VII" has been corrected so that this number is properly shown below the structure and not to the upper right.

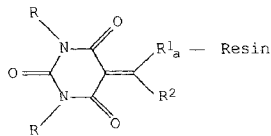

VII

Signed and Sealed this

Fifth Day of October, 2004

JON W. DUDAS
*Director of the United States Patent and Trademark Office*